(12) United States Patent
Cantineau

(10) Patent No.: US 8,011,294 B2
(45) Date of Patent: Sep. 6, 2011

(54) METHOD FOR HARVESTING BIOLOGICS FROM EGGS

(75) Inventor: Paul Cantineau, Le Vaudreuil (FR)

(73) Assignee: Sanofi Pasteur, Inc., Swiftwater, PA (US)

( * ) Notice: Subject to any disclaimer, the term of this patent is extended or adjusted under 35 U.S.C. 154(b) by 366 days.

(21) Appl. No.: 12/171,087

(22) Filed: Jul. 10, 2008

(65) Prior Publication Data

US 2009/0053803 A1 Feb. 26, 2009

Related U.S. Application Data

(60) Provisional application No. 60/948,982, filed on Jul. 10, 2007.

(51) Int. Cl.
*A23J 1/00* (2006.01)

(52) U.S. Cl. .............. 99/576; 99/496; 99/509; 99/537; 99/580

(58) Field of Classification Search .................. 426/614; 99/537, 576, 509, 580, 496; 435/349, 309.1
See application file for complete search history.

(56) References Cited

U.S. PATENT DOCUMENTS

| | | | | |
|---|---|---|---|---|
| 2,524,844 A * | 10/1950 | Smith | | 99/509 |
| 3,958,505 A | 5/1976 | Baker | | 99/495 |
| 3,973,482 A | 8/1976 | Khee | | 99/537 |
| RE33,164 E | 2/1990 | Brown et al. | | 424/89 |
| 5,197,380 A * | 3/1993 | Fisher | | 99/580 |
| 5,325,768 A | 7/1994 | van den Hazel | | 99/498 |
| 5,628,246 A | 5/1997 | Kristensen | | 99/500 |

FOREIGN PATENT DOCUMENTS

| | | | |
|---|---|---|---|
| JP | 7-203947 | * | 8/1995 |
| JP | 9-28302 | * | 2/1997 |

OTHER PUBLICATIONS

English machine translation for JP 9-280302 published Feb. 1997 from http://www4.ipdl.inpuit.go.jp.*
English machine translation for JP 7-203947 published Aug. 1995 from http://www4.ipdl.inpuit.go.jp.*
International Search Report and Written Opinion in PCT/US2008/069660 dated Jan. 28, 2009.
Bardiya et al., *Influenza vaccines: recent advances in production technologies*, Appl. Microbiol. Biotechnol. (2005) 67, pp. 299-305.

* cited by examiner

*Primary Examiner* — Anthony Weier
(74) *Attorney, Agent, or Firm* — Hulbert Boehnen Hulbert & Berghoff LLP

(57) ABSTRACT

A method for harvesting biologics from eggs by which an egg is de-capped by positioning the egg in a reference opening so as to expose an upper section of said egg, then, while said egg is positioned within the reference opening, cutting the upper section of the egg by moving a cutter member over the reference opening through the egg, and then removing the debris formed from the cut upper section. The biologics can then be harvested in various ways such as by inverting the egg to allow the biologics to drain for collection. An apparatus for carrying out the method is also provided.

12 Claims, 25 Drawing Sheets

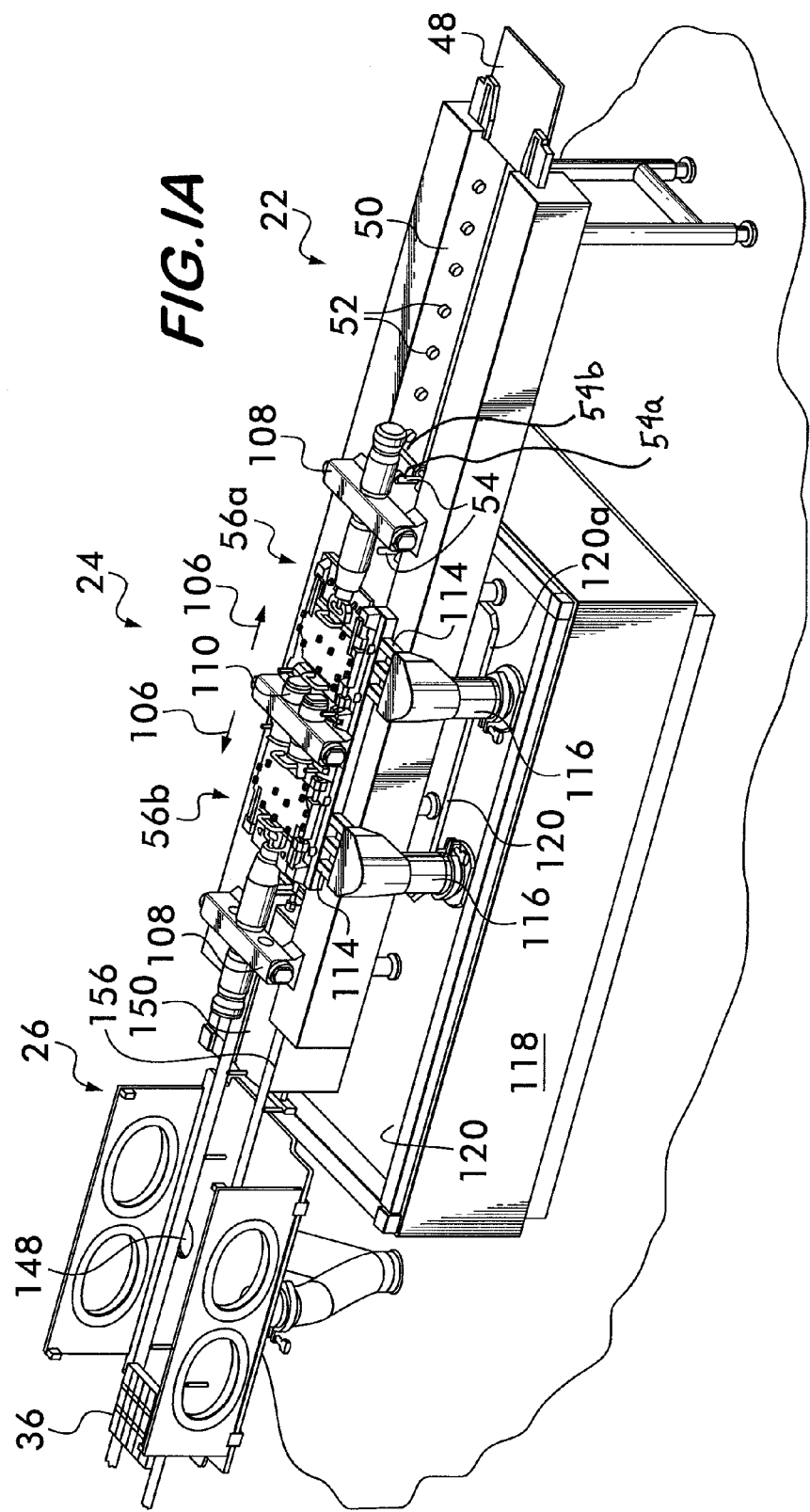

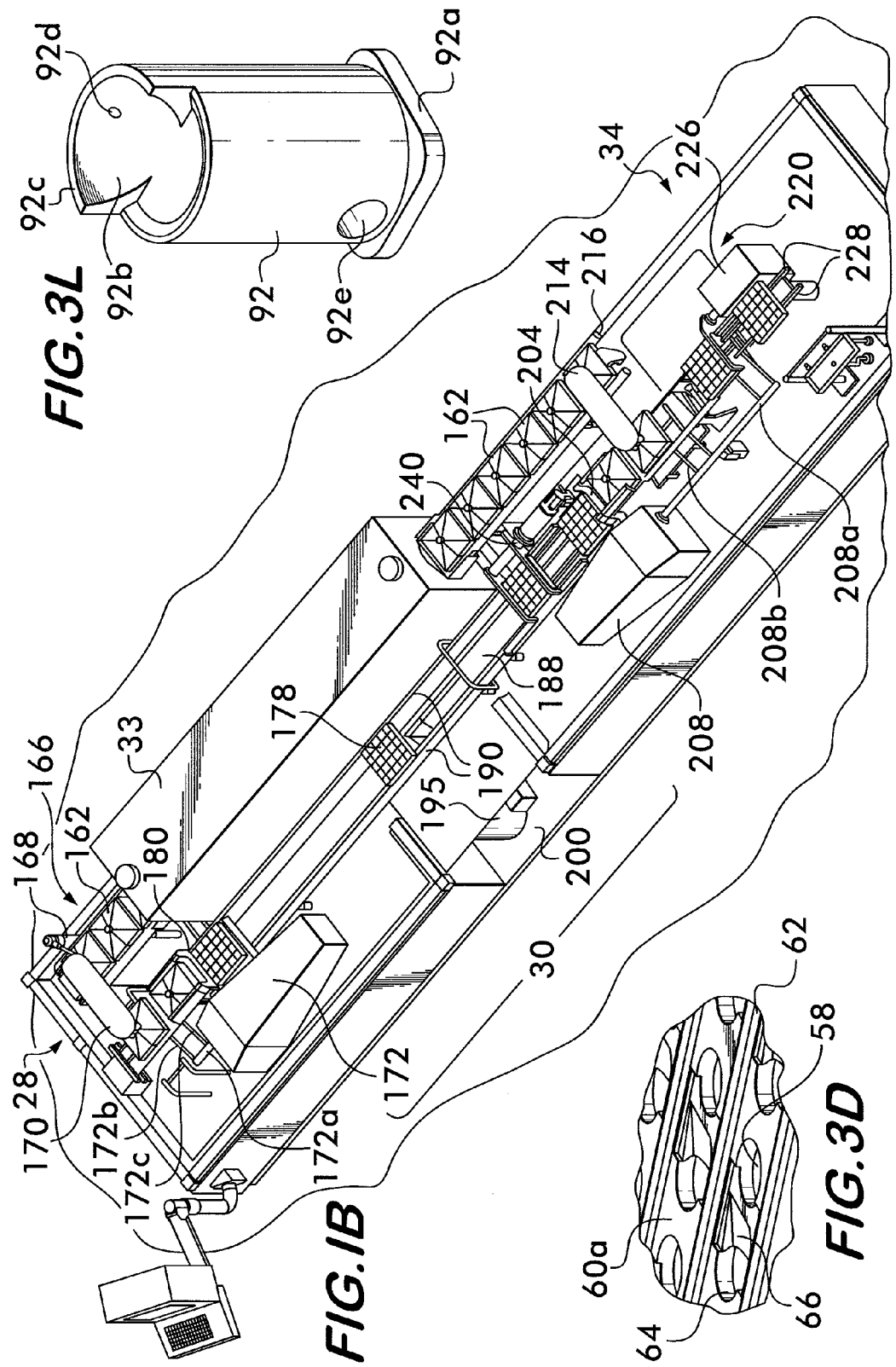

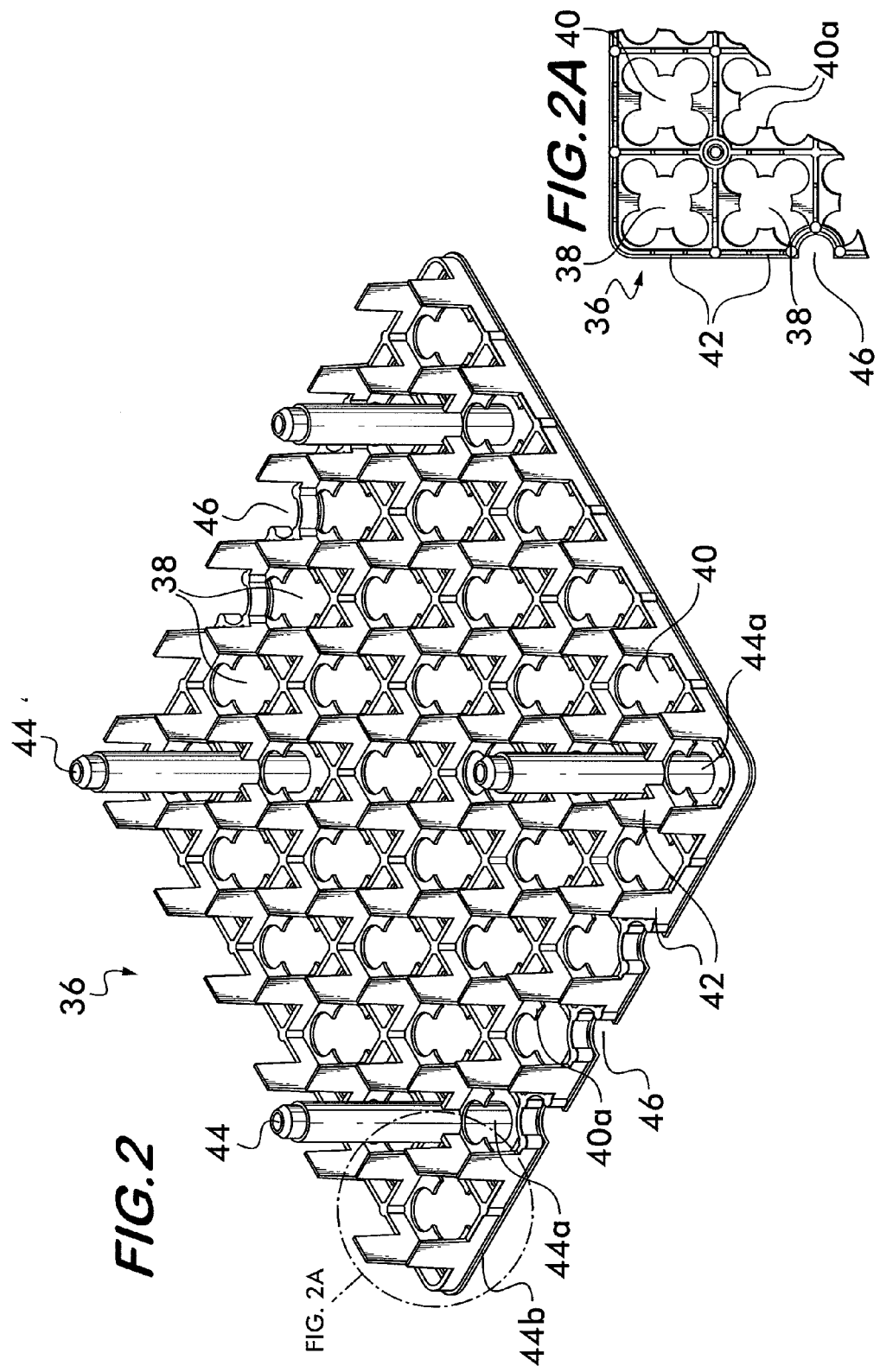

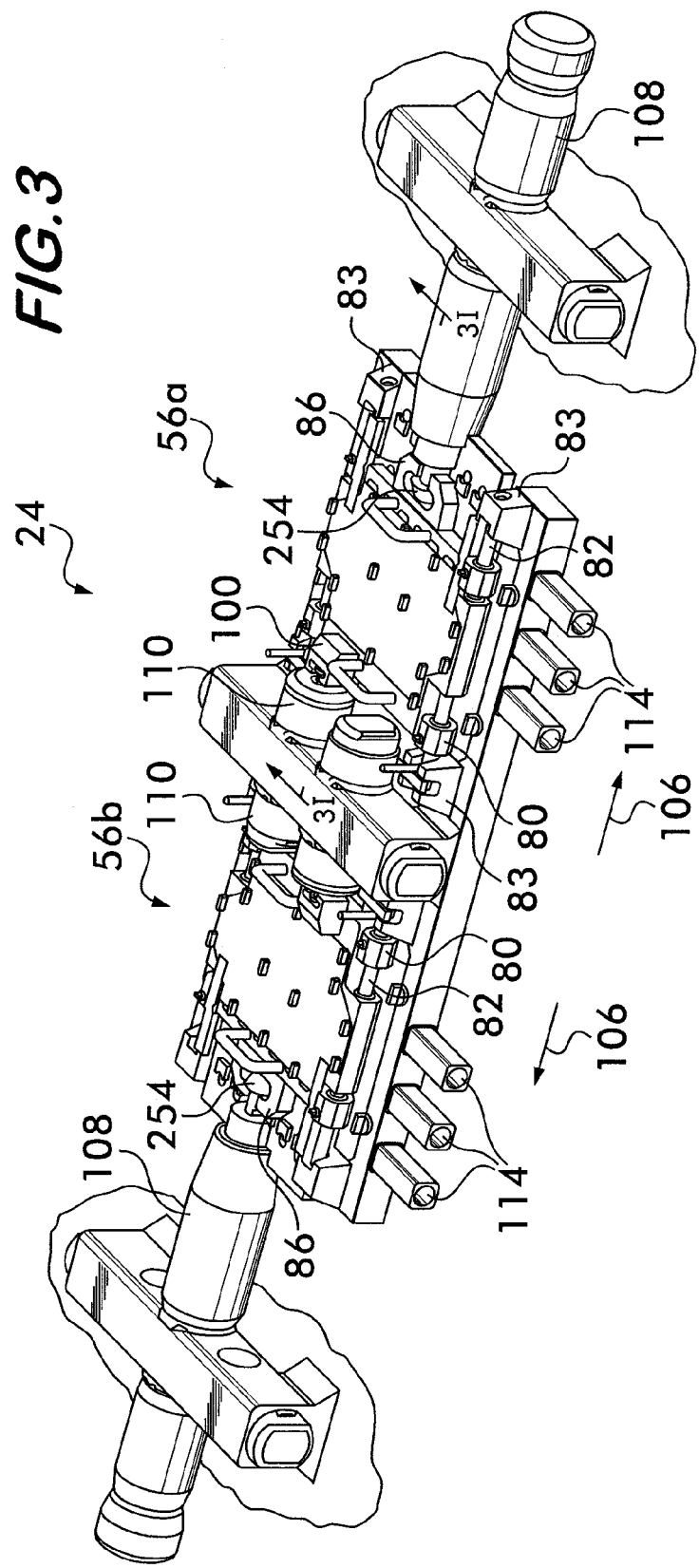

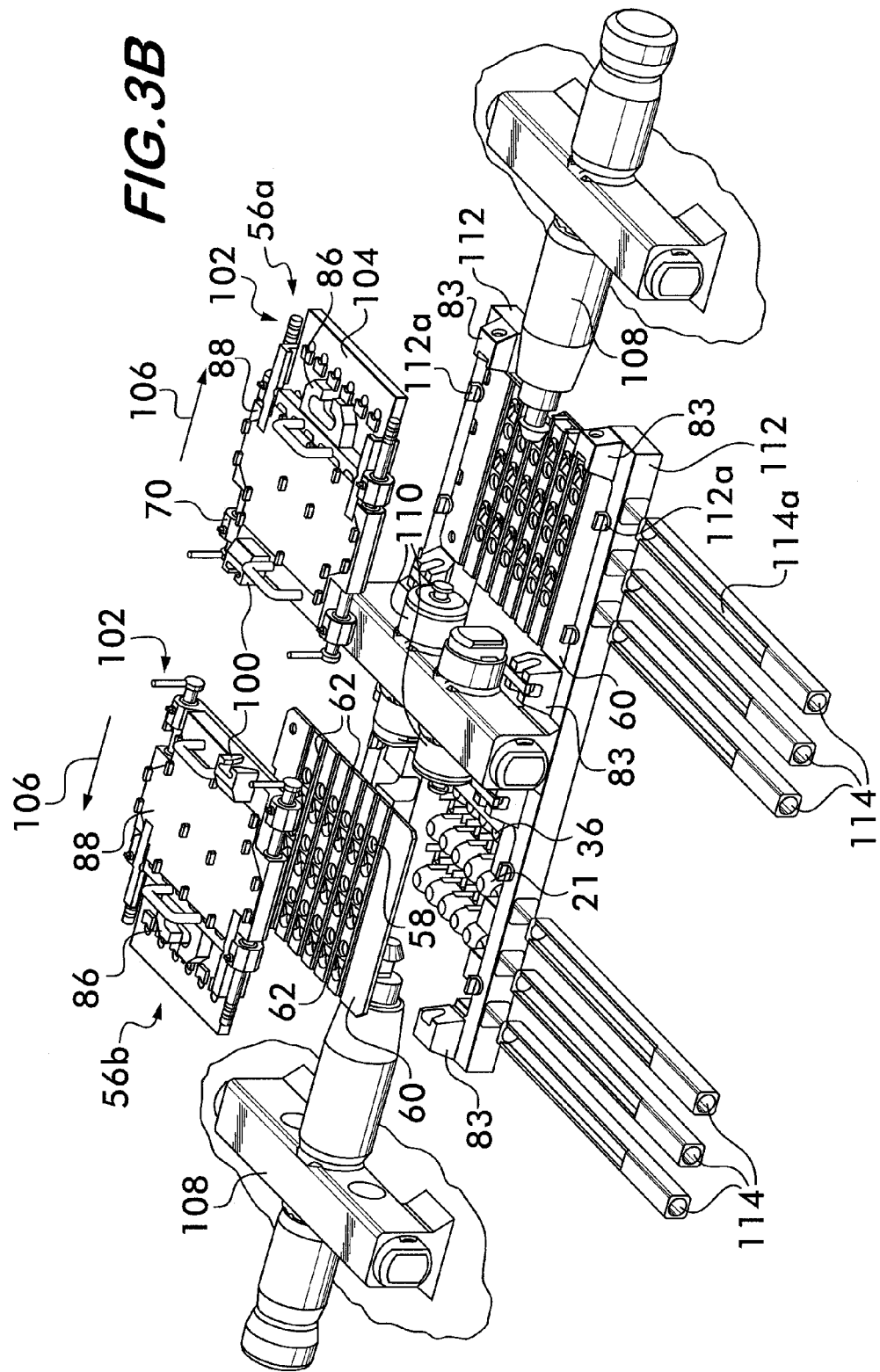

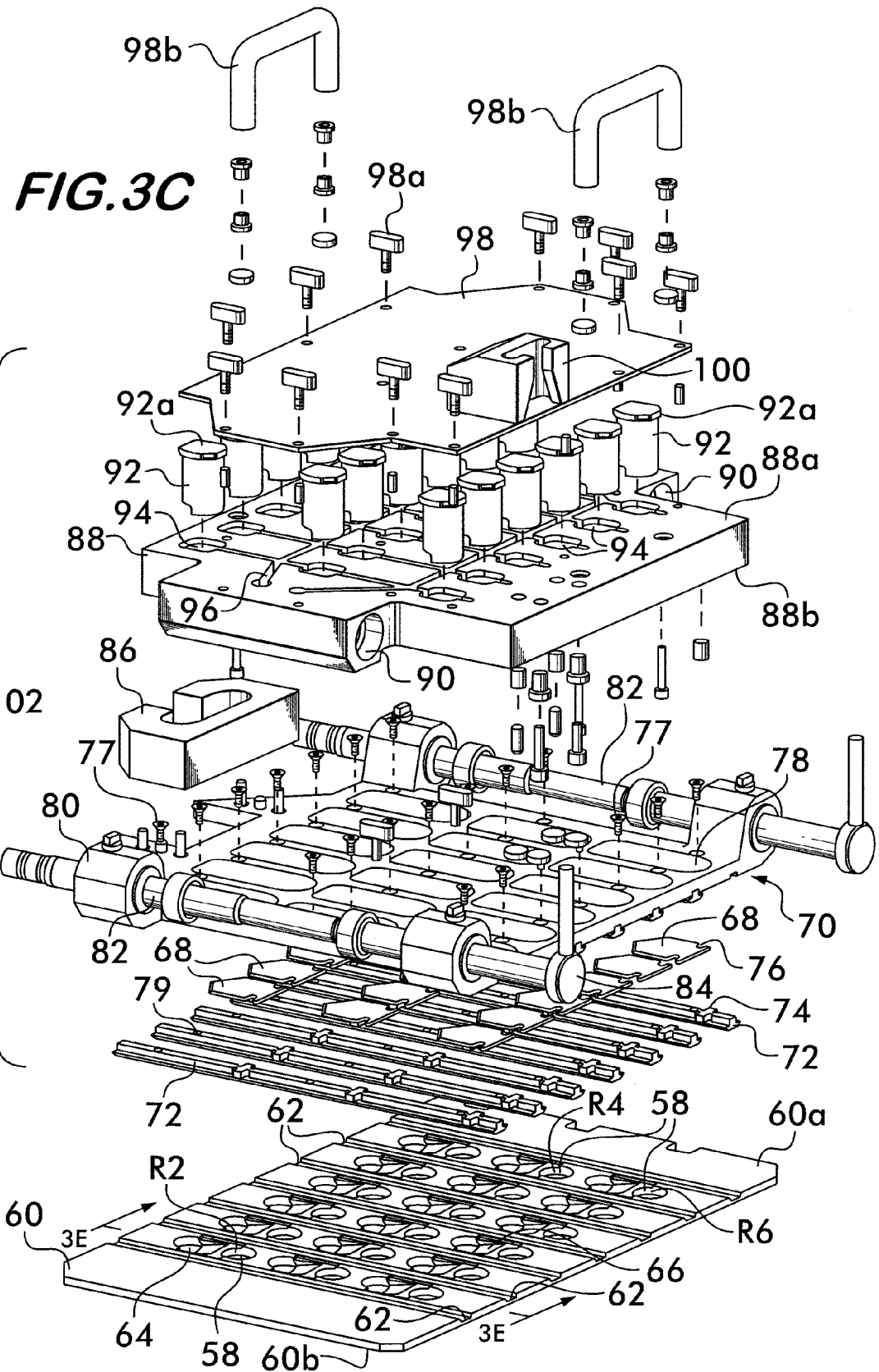

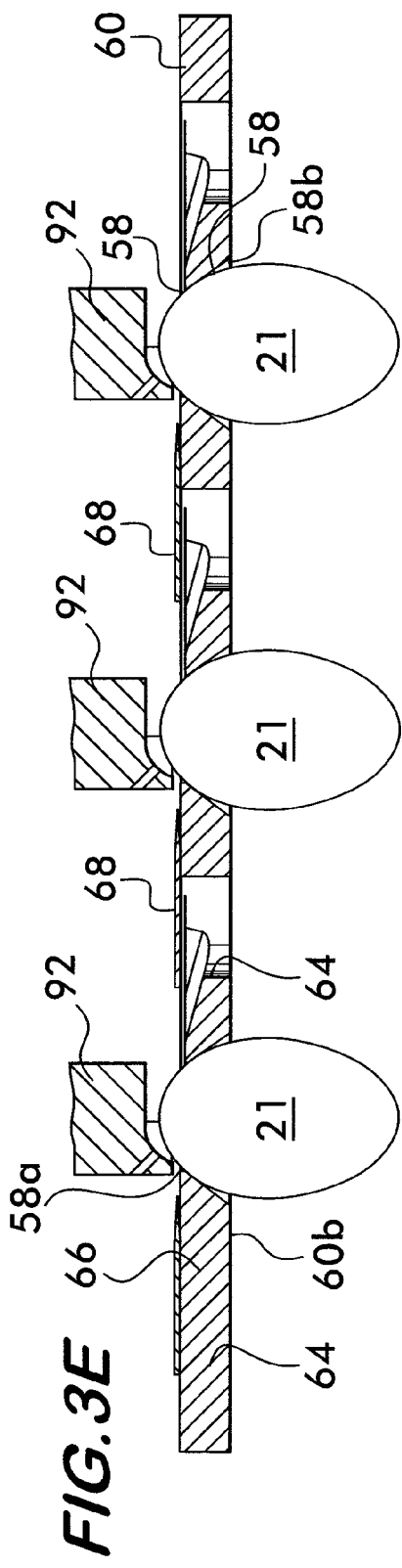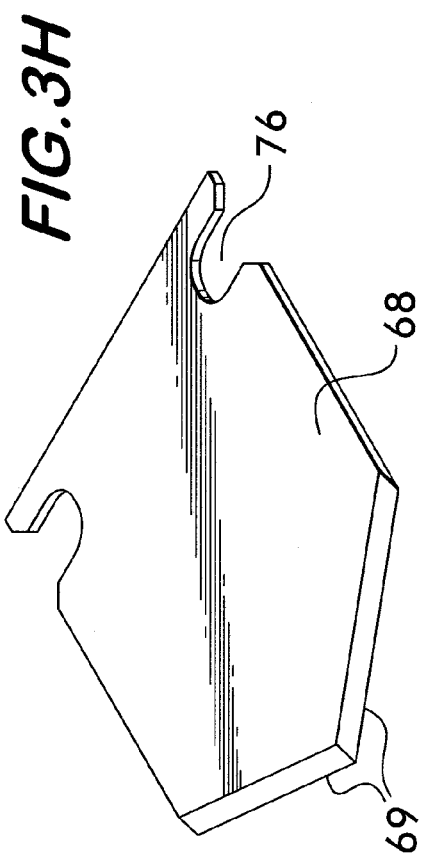

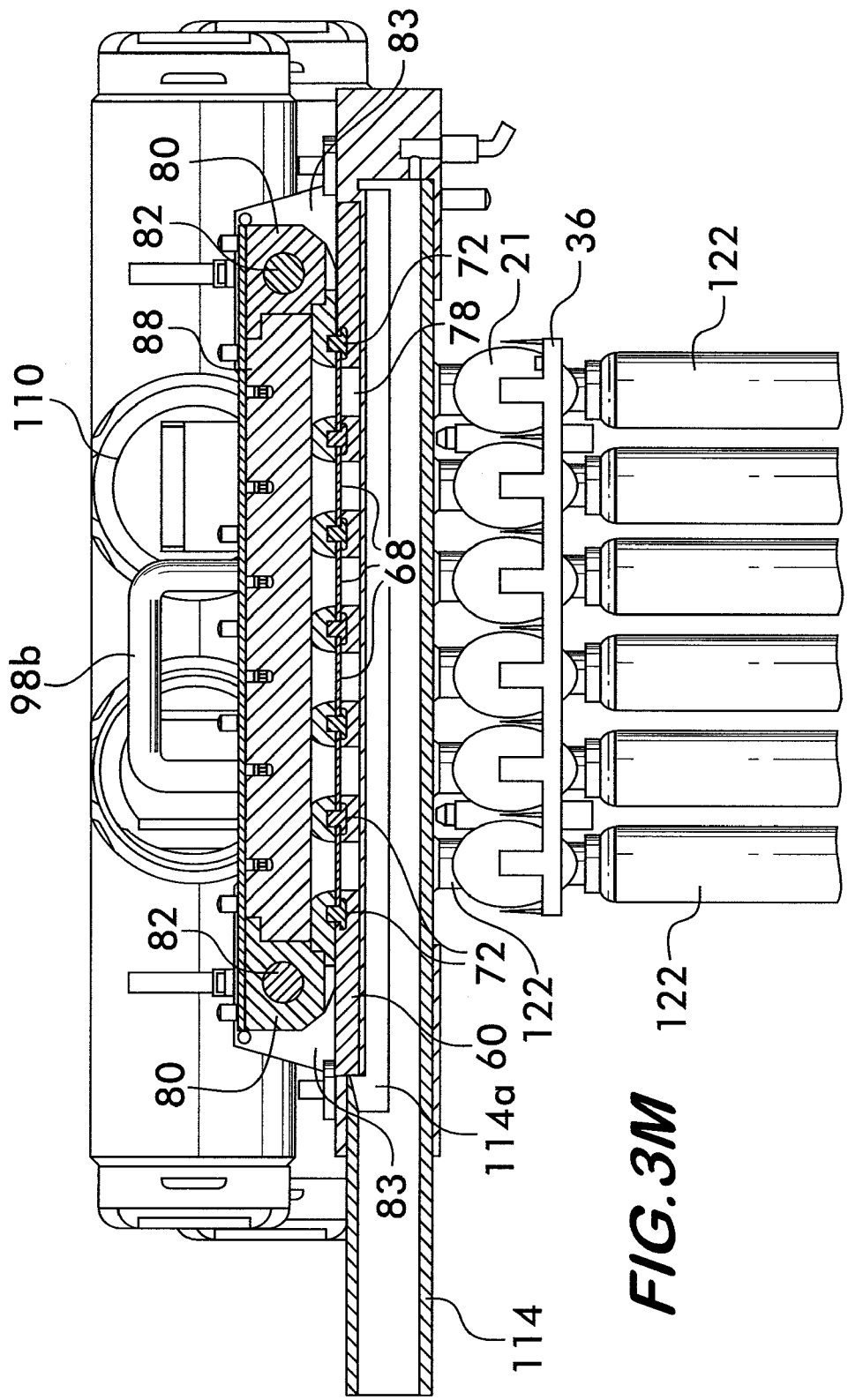

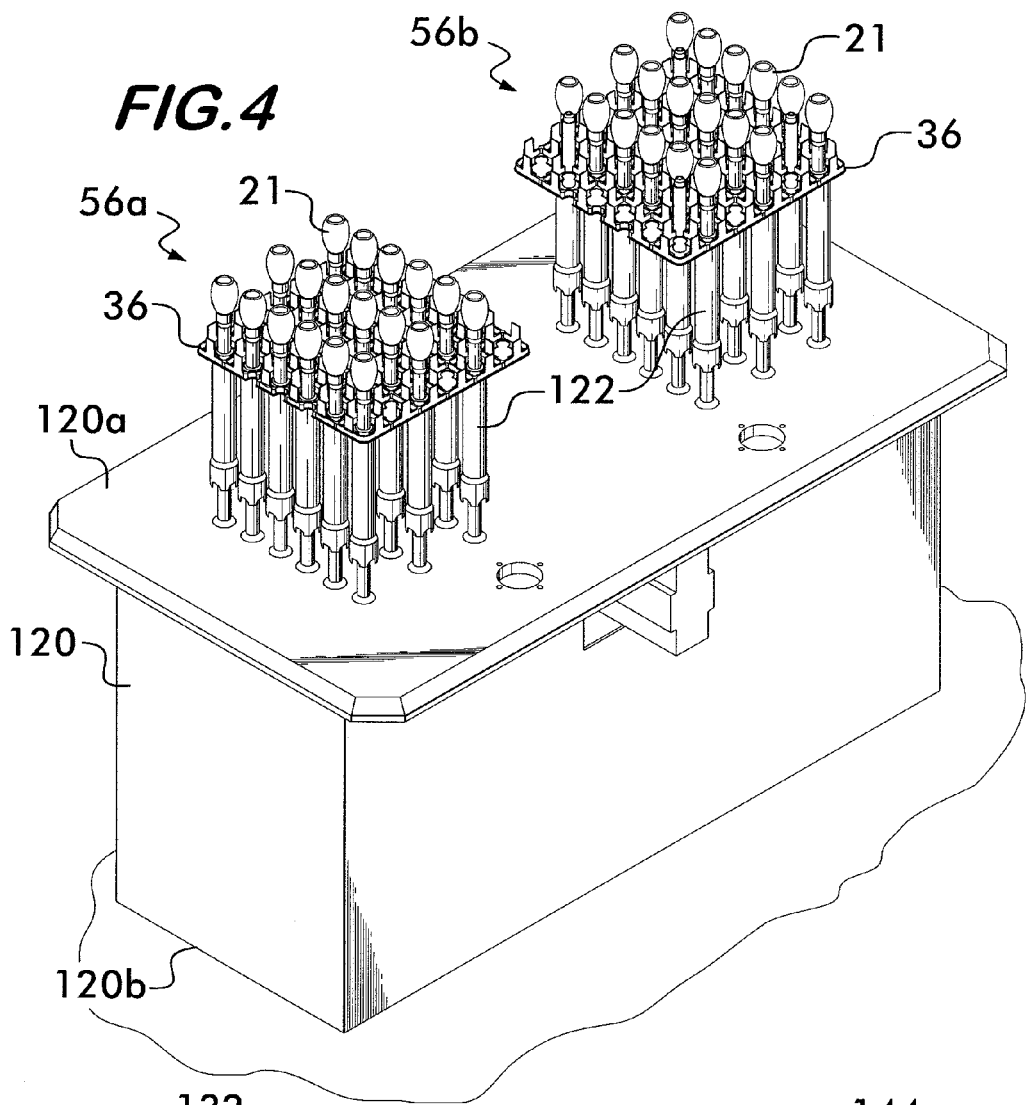
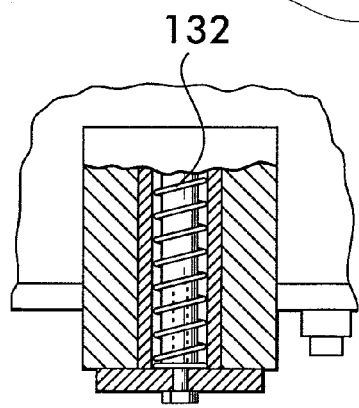
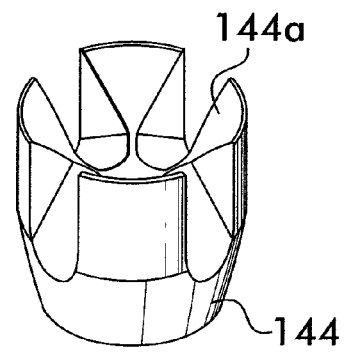

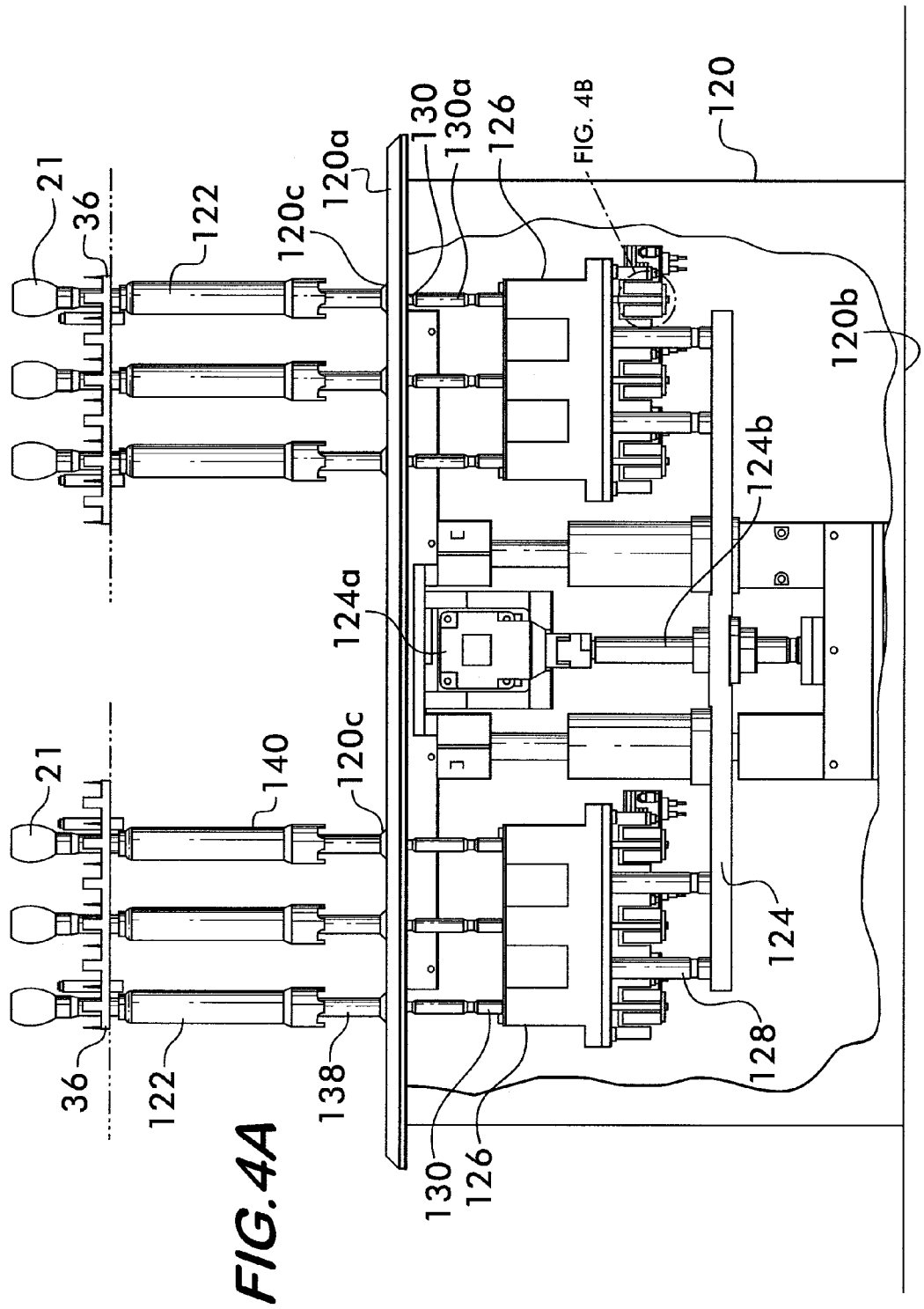

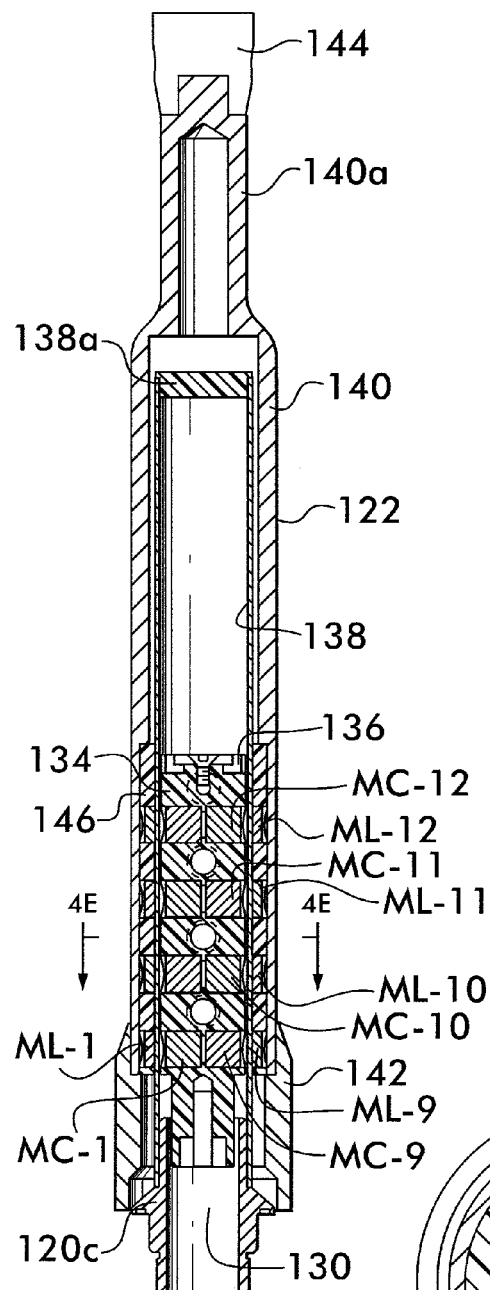
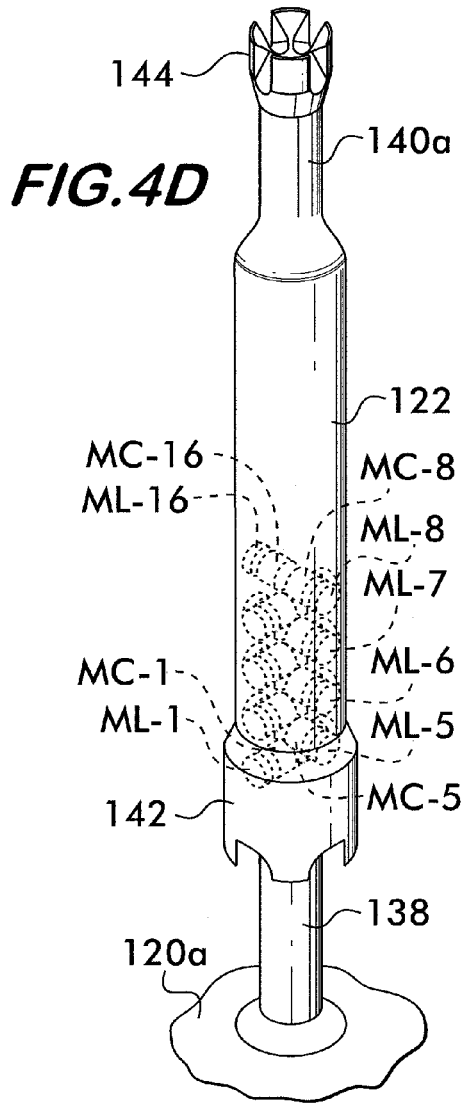
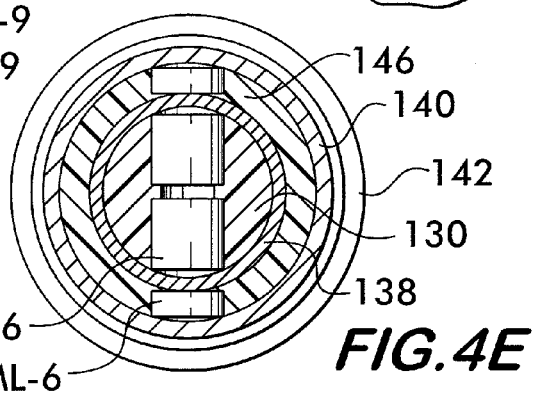
FIG.4C
FIG.4D
FIG.4E

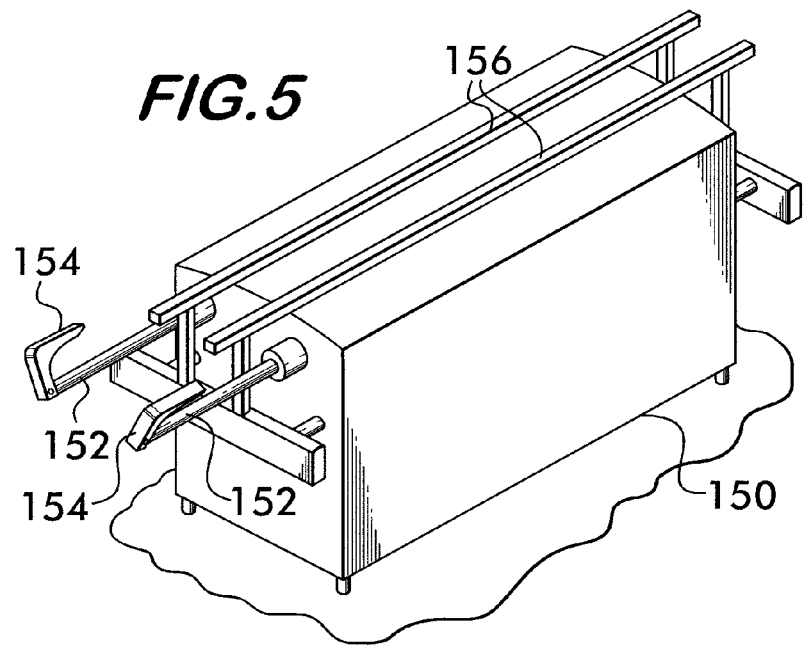
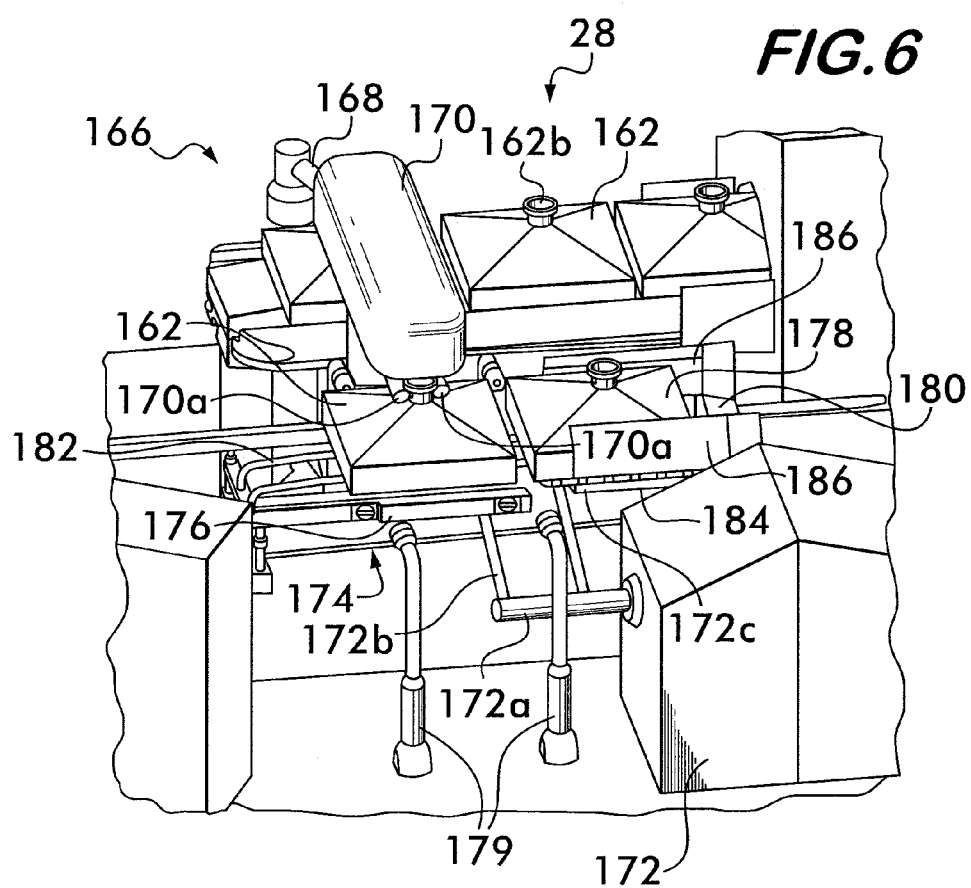

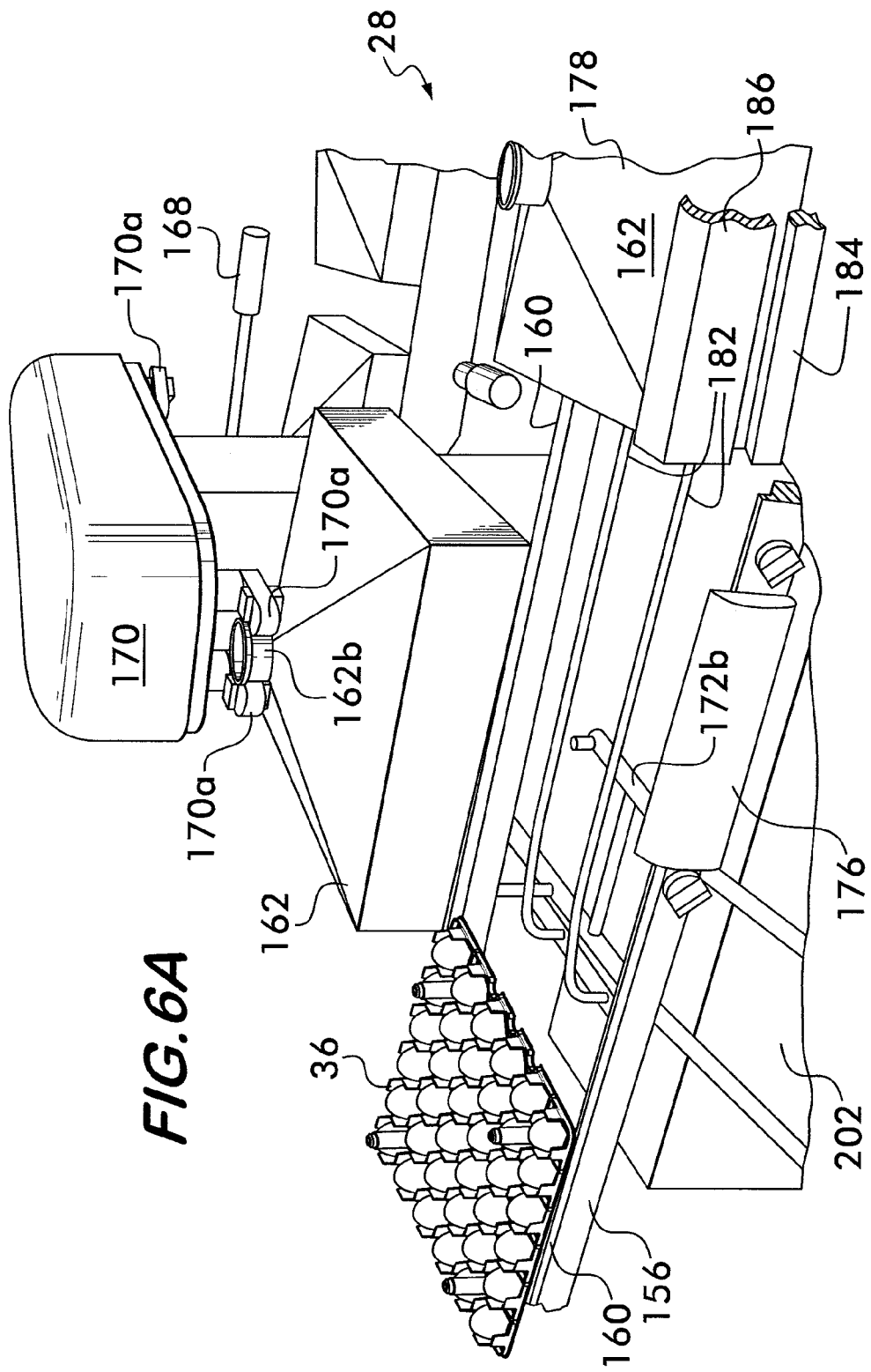

METHOD FOR HARVESTING BIOLOGICS FROM EGGS

CROSS REFERENCE TO RELATED APPLICATIONS

This application claims priority to U.S. Provisional Application No. 60/948,982 filed 10 Jul. 2007 and which is hereby incorporated herein by reference.

BACKGROUND

The present invention relates to the production of biologics such as viruses for vaccines, and more particularly to the harvesting of such biologics from eggs. Specifically, the present invention relates to apparatuses and methods for opening avian eggs and removing the desired biologics from within.

One method of producing biologics is to use fertilized avian eggs. The desired biologics are grown within the egg and must be harvested therefrom for further processing. Although a preferred embodiment of the present invention is directed to biologics such as viruses, the invention is believed to be applicable to other biologics that can be grown in eggs, such as proteins.

One method of producing vaccines, such as influenza vaccines, is to use fertilized avian (chicken) eggs. The eggs are injected with the viruses and, after a sufficient time of incubation to allow the virus to multiply, the eggs are opened to harvest the viruses.

Harvesting typically involves the collection of the allantoic fluid that is contained in the allantoic sac of a fertilized egg. It is preferable to harvest just the allantoic fluid and avoid contamination from the embryo containing yoke. The viruses are then separated from the fluid, purified, and inactivated to produce the final vaccine as is known in the art.

There are various methods for removing the allantoic fluid. One is to take advantage of the air sac within the top section of the egg shell. The top section, also referred to herein as the "egg cap", can be cut to provide access to the allantoic fluid within. Various means can be utilized to remove the allantoic fluid for further processing.

As can be appreciated, it is desirable to be able to produce large quantities of vaccines as fast as possible. The present invention provides an advantageous apparatus and method for harvesting the allantoic fluid for producing vaccines.

Embryonated eggs have proven to be a useful medium for the isolation and identification of animal viruses, for titrating viruses, and for cultivation of viruses in the production of viral vaccines. The embryo, chorioallantoic membrane, yolk sac, allantoic sac, and amniotic sac may be inoculated in eggs at various developmental stages providing the scientist with large array of tissue types for specific purposes.

The apparatus and method of the present invention can be adapted for recovering a number of biologically active molecules from the components of embryonated avian eggs (e.g., allantoic fluid, embryo, chorioallantoic membrane, etc.) in addition to the influenza virus. Exemplarily biologically active molecules that may harvested from avian eggs components include viruses and immunoglobulins such as, but not limited to, flaviviruses (e.g., yellow fever virus); arboviruses (e.g., Sindbis virus, Murray Valley encephalitis virus, and Getah virus); orbiviruses (e.g., Bluetongue virus); aphtoviruses (e.g., type C foot-and-mouth-disease virus); alpharetrovirus (e.g., avian leukosis virus); gammaretrovirus (e.g., reticuloendotheliosis virus); rubulavirus (e.g., mumps virus and Newcastle disease virus); avian adenovirus (e.g., chicken embryo lethal orphan virus (CELO) and related quail bronchitis virus); infectious bronchitis the virus; and immunoglobulins from aves inoculated with a variety of infectious agents and/or antigens.

The production of viruses for influenza vaccine production is one preferred use of the present invention. The influenza viruses are some of the most ubiquitous viruses present in the world, affecting both humans and livestock. Influenza infections result in an economic burden, severe morbidity, and even death in the very young, the elderly and immunocompromised individuals. According to statistics from the World Health Organization, looking just at the U.S.A., there are 25-50 million cases of influenza resulting in approximately 150,000 hospitalizations and from 30,000-40,000 deaths per year. The world inter-pandemic influenza burden may be as high as 1 billion cases of influenza with 3-5 million cases of severe illness. Extrapolation of these statistics predicts from 300,000-500,000 annual deaths attributed to influenza worldwide.

Influenza viruses are spread from person to person, primarily through direct respiratory droplet transmission (e.g., when an infected person coughs or sneezes in close proximity to an uninfected person). Indirect transmission is also possible and usually results from tactical transfer (e.g., handshake) of contaminated secretion from an infected person to an uninfected person's nasal or conjunctival epithelium.

The typical incubation period for influenza is one to four days, with an average of two days. Adults can be infectious from the day before symptoms begin through approximately five days after illness onset. Children can be infectious for >10 days after the onset of symptoms, and young children also can shed virus before onset of illness. Severely immunocompromised persons can shed virus for weeks or even months after infection.

Uncomplicated influenza illness is characterized by the abrupt onset of constitutional and respiratory signs and symptoms (e.g., fever, myalgia, headache, malaise, nonproductive cough, sore throat, and rhinitis). Among children, otitis media, nausea, and vomiting also are commonly reported with influenza illness. Uncomplicated influenza illness typically resolves after three to seven days for the majority of persons, although cough and malaise can persist for >2 weeks. However, among certain persons, influenza can exacerbate underlying medical conditions (e.g., pulmonary or cardiac disease), lead to secondary bacterial pneumonia or primary influenza viral pneumonia, or occur as part of a coinfection with other viral or bacterial pathogens. Young children with influenza virus infection can have initial symptoms mimicking bacterial sepsis with high fevers, and febrile seizures have been reported in up to 20% of children hospitalized with influenza virus infection. Influenza virus infection also has been uncommonly associated with encephalopathy, transverse myelitis, myositis, myocarditis, pericarditis, and Reye syndrome.

Accordingly, improved methods and apparatuses for producing vaccines are desired.

Preferred embodiments of the present invention relate to methods and apparatuses for separating the components of avian eggs. Eggs suitable for use in the methods and apparatuses of the present invention can be obtained from a number of avian species including, but not limited to, domesticated chickens (gallus), turkeys, geese, ducks, quail, and the like. The present invention is primarily used to collect allantoic fluid from embryonated chicken eggs, however, the disclosed apparatuses and methods are useful for separating yolk and embryo from embryonated eggs as well. The embryogenesis of chick egg development is well characterized in the art. The reader is referred to standard texts in the field of chick development for additional details of the structures and development of chick embryos (e.g., R. Bellairs and M. Osmund, The Atlas of Chick Development, 2nd ed., Elsevier, New York N.Y., 2005).

The allantoic fluid from avian eggs, in particular chicken eggs, can be inoculated with live virus from the othomyxoviridae family. The inoculated virus replicates in the egg while the eggs are incubated from two to three days depending on the viral strain used for inoculation. The influenza virus is subsequently isolated and purified from the allantoic fluid collected from the inoculated eggs.

The othomyxoviridae family includes four genera: influenza A, influenza B, influenza C, and thogotovirus (sometimes called influenza D). Influenza A and B are responsible for most epidemic human disease. Influenza A also infects swine, horses, sea mammals, and birds, including, domesticated poultry and waterfowl. Human infection with influenza A usually results in more sever disease symptoms than those following infection with the other genera of influenza. Influenza A is also the most disposed to significant antigenic changes from season to season through antigen drifts and antigenic shift. Influenza B appears to only infect humans. Influenza C has been isolated from both swine and humans it is thought to cause only mild respiratory illness and not epidemics. Thogotoviruses are tick born viruses which are genetically and structurally related to the influenza A, B, and C viruses.

All othomyxoviridae viruses are enveloped viruses with a negative single stranded RNA (nsRNA) genome. In particular, influenza A and B viruses each contain eight segments of nsRNA enveloped in a glycolipid membrane derived from the host cell's plasma membrane. More particularly, the influenza A and B viral genome consists of segments PB2, PB1, PA, NP, M, NS, HA and NA) that encode at least 10 polypeptides, including RNA-directed RNA polymerase proteins (PB2, PB1 and PA), nucleoprotein (NP), neuraminidase (NA), hemagglutinin (subunits HA1 and HA2), the matrix proteins (M1 and M2) and the non-structural proteins (NS1 and NS2) (Krug et al., In The Influenza Viruses, R. M. Krug, ed., Plenum Press, N.Y., 1989, pp. 89-152).

The inner surface of the glycolipid membrane contains virus specific proteins while the exterior surface is studded with virus specific neuramidase (NA) and hemagglutinin (HA) proteins. HA was named for its ability to agglutinate erythrocytes (red blood cells) by attaching to N-acetylneuraminic (sialic) acid containing glycoprotein or glycolipid receptor sites on the surface of respiratory epithelial cells. HA is also responsible for facilitating penetration of the influenza virus particle into the cell's cytoplasm by mediating fusion of the virus particle membrane with the cell's membrane of the endosome encapsulating the virus particle with the consequence being the subsequent release of the viral nucleocapsids into the cell's cytoplasm. The nucleocapsid segments contain the viral genetic material destined for migration into the cell's nucleus. The acidic interior of the endosome encapsulating the virus particle causes the HA to slightly alter its structure and merge with the endosomal membrane until a hole is formed in the endosome. Major epidemics are associated with changes in the antigenic structure of HA and it is also the principal viral antigen against which infected hosts produce neutralizing antibodies. HA is the most important antigen in defining the serological specificity of the different influenza strains. This 75-80 kD protein contains numerous antigenic determinants, several of which are in regions that undergo sequence changes in different strains (strain-specific determinants) and others in regions which are common to many HA molecules (common to determinants).

NA is a hydrolytic enzyme that removes the terminal sialic acid from the cell's hemagglutinin receptors resulting in destruction of the receptor activity. The roles NA plays in influenza infection are not completely understood, however it is thought that NA may allow the virus particle to penetrate the mucin layer in respiratory tract that would otherwise bind virus particles and prevent them from contacting the surface of respiratory epithelial cells. NA may also be important in the fusion of the virus particle with the cell membrane prior to viral entry into the cell.

Influenza C virus is also enveloped with a nsRNA genome. The genome is composed of only seven RNA segments however and it has only a single multifunctional surface glycoprotein called hemagglutinin-esterase-fusion protein (HEF). As the names implies, the HEF protein has three functions a receptor-binding activity, a fusion activity, and a receptor-destroying activity.

Both influenza A and B viruses are further separated into groups on the basis of antigenic characteristics. Influenza A viruses are divided into subtypes based on two proteins on the surface of the virus: the hemagglutinin (H) and the neuraminidase (N). There are 16 different hemagglutinin subtypes and 9 different neuraminidase subtypes, all of which have been found among influenza A viruses in wild birds. Wild birds are the primary natural reservoir for all subtypes of influenza A viruses and are thought to be the source of influenza A viruses in all other animals. Most influenza viruses cause asymptomatic or mild infection in birds. Infection with certain avian influenza A viruses (for example, some strains of H5 and H7 viruses) can cause widespread disease and death among some species of wild and especially domestic birds such as chickens and turkeys. Only one subtype of HA and one of NA are recognized for influenza B viruses.

Influenza viruses can change in two different ways. One is called "antigenic drift." These are small changes in the virus that happen continually over time. Antigenic drift produces new virus strains that may not be recognized by the body's immune system. This process works as follows: a person infected with a particular flu virus strain develops antibody against that virus. As newer virus strains appear, the antibodies against the older strains no longer recognize the "newer" virus, and reinfection can occur. This is one of the main reasons why people can get the flu more than one time. In most years, one or two of the three virus strains in the influenza vaccine are updated to keep up with the changes in the circulating flu viruses. So, people who want to be protected from flu need to get a flu shot every year.

The other type of change is called "antigenic shift." Antigenic shift is an abrupt, major change in the influenza A viruses, resulting in new hemagglutinin and/or new hemagglutinin and neuraminidase proteins in influenza viruses that infect humans. Shift results in a new influenza A subtype. When shift happens, most people have little or no protection against the new virus. While influenza viruses are changing by antigenic drift all the time, antigenic shift happens only occasionally. Type A viruses undergo both kinds of changes; influenza type B viruses change only by the more gradual process of antigenic drift.

Pigs can be infected with both human and avian influenza viruses in addition to swine influenza viruses. Infected pigs get symptoms similar to humans, such as cough, fever, and runny nose. Because pigs are susceptible to avian, human and swine influenza viruses, they potentially may be infected with influenza viruses from different species (e.g., ducks and humans) at the same time. If this happens, it is possible for the genes of these viruses to mix and create a new virus. For example, if a pig were infected with a human influenza virus and an avian influenza virus at the same time, the viruses could mix (reassort) and produce a new virus that had most of the genes from the human virus, but a hemagglutinin and/or neuraminidase from the avian virus. The resulting new virus would likely be able to infect humans and spread from person to person, but it would have surface proteins (hemagglutinin and/or neuraminidase) not previously seen in influenza viruses that infect humans. This type of major change in the influenza A viruses is known as antigenic shift. Antigenic shift results when a new influenza A subtype to which most people have little or no immune protection infects humans. If this new virus causes illness in people and can be transmitted easily from person to person, an influenza pandemic can occur.

The term "avian" as used herein, is intended to include males and females of any avian species, but is primarily intended to encompass domestic poultry which is commercially raised for eggs, meat, or as pets. The term "avian" is particularly intended to encompass various avian species including, but not limited to, chickens, turkeys, ducks, geese, quail, pheasant, ostrich, and, emu, etc. Accordingly, the term "avian egg" refers to an embryonated egg laid by a female of one of the aforementioned avian species, and more preferably to an embryonated egg from a chicken.

As used herein, the term "membrane" refers to any layer of tissue within an egg that delimits an internal structure or area within the egg. Exemplary membranes within an egg include, but are not limited to, the outer shell membrane, inner shell membrane, the chorioallantoic membrane (CAM), vitelline membrane (VM), and amniotic membrane (amnion).

The present invention, which will now be described in detail below, provides novel methods and apparatuses for harvesting biologics from eggs.

SUMMARY OF THE INVENTION

In broad terms, the invention provides a method for opening an egg. This includes positioning the egg in a reference opening so as to expose a section of egg to be opened; then, while the egg is positioned within the reference opening, creating an opening in the exposed section of egg by moving a cutter member over the reference opening into the egg; and then removing egg debris formed when opening said egg. Once the egg is opened, fluids from the egg can be collected by inverting the egg to allow the fluids to drain therefrom, and then collecting the fluids.

The invention also provides a method of collecting fluid from multiple eggs. In one form, the invention provides for moving at least a portion of the multiple eggs upwardly into reference openings, each of the reference openings being configured to expose a predetermined approximate amount of egg to be removed for opening said eggs; then moving a cutter member into said eggs to create openings in the eggs; inverting the opened eggs to allow fluid from within the eggs to drain therefrom; and then collecting the drained fluid.

An apparatus for carrying these methods is also provided. In one form, such apparatus includes at least one de-cap apparatus having a reference plate with at least one reference opening therethrough, the opening being configured for receiving the egg therein from a lower side of the plate and for stopping further upward movement of the egg within the opening when an upper egg section to be cut extends from the opening above the first plate; and a cutter member positioned above the reference plate wherein the cutter member is moveable across the reference opening so as to create an opening in the upper egg section. The apparatus further includes at least one tray configured for holding the multiple eggs therein; lifting arms configured to hold said eggs, the arms being operable to lift said eggs from said tray and move them to said de-cap unit and then return said eggs to said tray; a drainage pan configured to be combined with said tray to form a tray/pan assembly; an invert unit for inverting the tray/pan assembly so that the openings of the eggs therein face downward to allow the fluid to drain therefrom; a drainage trough for collecting draining fluids from the inverted eggs, the inverted tray/pan assembly being moveable over the trough; and a transport system for moving the tray and tray/pan assembly through the apparatus.

The apparatus and method of the present invention are useful for collecting viral laden allantoic fluid from avian eggs. The viral laden allantoic fluid can be subsequently processed using one or more clarification, centrifugation, purification, splitting, inactivating and/or adjuventation steps known in the art and routinely used in the production of immunogenic compositions and/or vaccines. In preferred embodiments, the influenza virus laden allantoic fluid collected according to the present invention is subsequently processed according to routine methods known in the art for producing influenza vaccines.

BRIEF DESCRIPTION OF THE FIGURES

The following detailed description will be better understood when read in conjunction with the figures appended hereto. For the purpose of illustrating the invention, there is shown in the drawings a preferred embodiment. It is understood, however, that this invention is not limited to this embodiment or the precise arrangements shown.

FIG. 1A is a partial enlarged isometric view of the apparatus shown in FIG. 1 shown from the opposite side;

FIG. 1B is a partial enlarged isometric view of the apparatus shown in FIG. 1;

FIG. 2 is an isometric view of an egg tray used with the present invention;

FIG. 2A is an enlarged partial plan view taken along circle 2A in FIG. 2;

FIG. 3 is an enlarged isometric view of the de-capping units of the apparatus shown in FIG. 1A;

FIG. 3B is an exploded isometric view of the de-capping units shown in FIG. 3;

FIG. 3C is an exploded isometric view of a reference plate, de-capping plate and debris wiper plate of one de-cap unit shown in FIG. 3B;

FIG. 3D is an enlarged isometric partial view of the reference plate shown in FIG. 3C;

FIG. 3E is a cross-sectional view taken a long line 3E-3E of the reference plate of FIG. 3C, and which further illustrates the position of the cutting blades, wiper caps, and eggs relative to the reference plate prior to the cutting of the eggs;

FIG. 3H is an isometric view of a blade of the de-cap plate;

FIG. 3L is a perspective view of a removal cap;

FIG. 3M is a cross sectional view taken along line 3M-3M of FIG. 3K;

FIG. 4 is an isometric view of the egg lifter assembly shown removed from the apparatus of FIG. 1;

FIG. 4A is a side view of the egg lifter assembly of FIG. 4 with the side wall of the table removed;

FIG. 4B is a cross sectional view of circle 4B in FIG. 4A showing a spring assembly;

FIG. 4C is a cross-sectional view of a lifter arm coupled to a coupling piston;

FIG. 4D is an isometric view of the lifter arm coupled to a coupling piston shown in FIG. 4C;

FIG. 4E is a cross-sectional view taken along line 4E-4E of FIG. 4C;

FIG. 4F is an isometric view of an egg support cup;

FIG. 5 is an isometric view of the tray pusher positioned down steam of the de-cap station.

FIG. 6 is an isometric view of the infeed pan and invert station;

FIG. 6A is a perspective view of the infeed pan and invert station of FIG. 6 viewed from another direction;

DETAILED DESCRIPTION OF THE INVENTION

Figure 1:
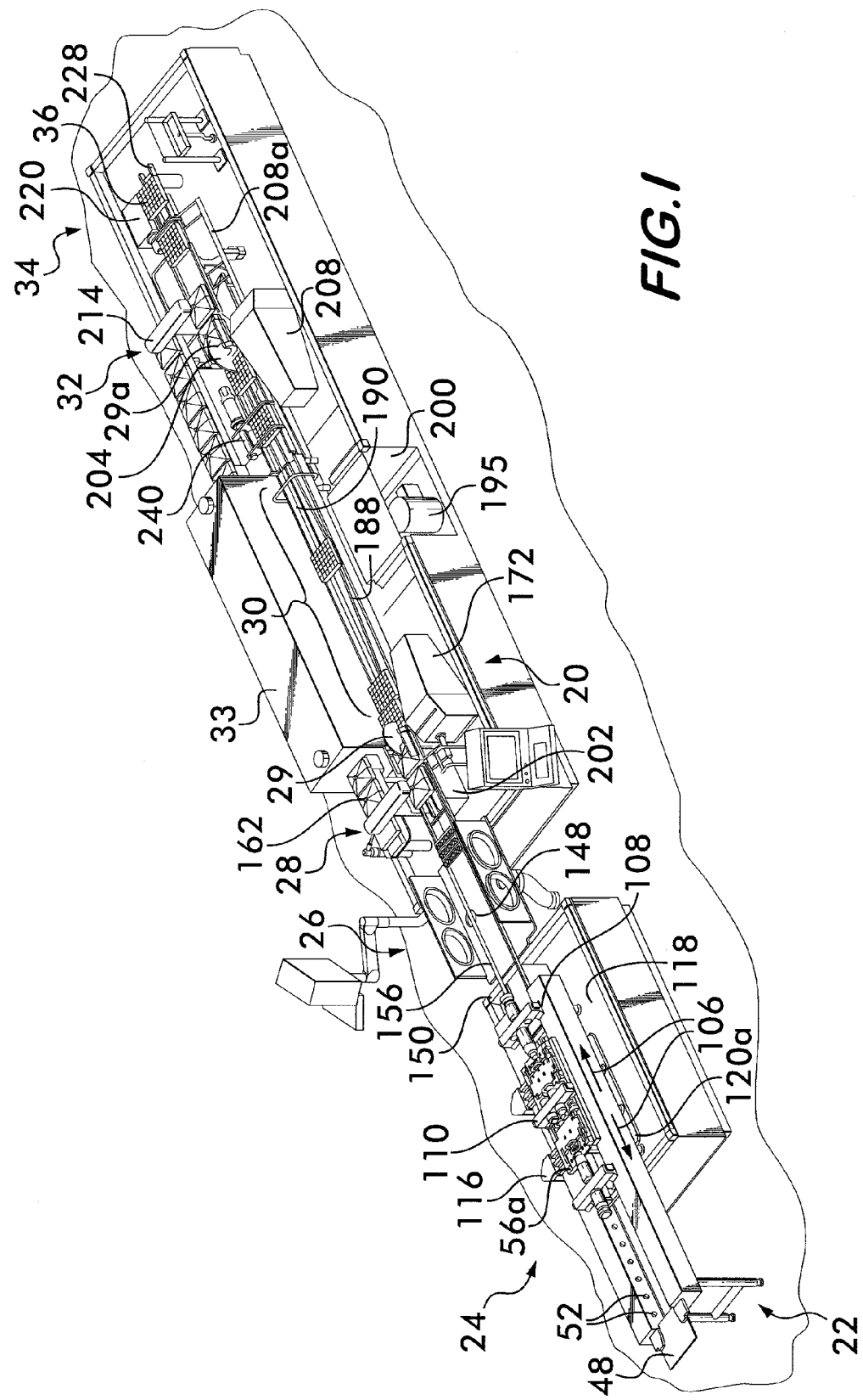
FIG. 1 is an isometric view of an apparatus for harvesting viruses from chicken eggs in accordance with the present invention.

The apparatuses and methods of the present invention will now be described with reference to the figures appended hereto. With initial reference to FIGS. 1, 1A and 1B, illustrated in the figures is an exemplary apparatus 20 for harvesting allantoic fluid from embryonated chicken eggs. FIG. 1 shows the overall apparatus, FIG. 1A shows the front section of the apparatus and FIG. 1B shows the mid and back sections of the apparatus 20. As will be described below in more detail, the apparatus 20 is formed of numerous sub-components and carries out numerous methods for completing the harvesting process. Many of these components and methods are believed to be novel in addition to the overall apparatus and process.

As is known in the art, the apparatus 20 is preferably enclosed within a clean environment, such as an enclosure of glass panels supplied with filtered air. Such enclosures are well known in the art and thus no further description is required. For purposes of describing the invention, the apparatus 20 can be broken down into major stations, each of which carries out a basic function or functions. A general description of the various stations is now provided, followed by a more detailed description of the individual stations.

An initial station is the egg loading station 22 or conveyor (left side of FIG. 1) where multiple eggs can be placed into the apparatus 20. Here, in the preferred embodiment, an operator manually loads trays 36 (FIG. 2) of eggs into the apparatus 20. Each tray 36 of eggs, thirty-six eggs per tray, is then moved towards the right through the apparatus 20 to the other stations for further processing.

In an egg de-cap station 24, an opening is created in the top portion of the egg shells (also referred to as "caps"). In the preferred embodiment described herein, the caps are cut and removed to create the opening in the eggs. The debris created by the opening process, e.g., the cut caps, is then discarded via a debris removal system.

The de-capped eggs are next inspected at an inspection station 26. Here, operators can manually inspect each egg, discard rejected eggs, and remove any un-cut eggs for reprocessing.

After the inspection station 26, the tray of de-capped eggs moves to an infeed pan and invert station 28 (FIG. 1). Here, a drain pan 162 for draining the allantoic fluid is placed on top of the tray 36. The combined tray/pan is then inverted at this station, turning the eggs so that the openings in the eggs face downward to allow the allantoic fluid to drain therefrom (the semicircle 29 in FIG. 1 represents the inversion motion).

Once inverted, the tray/pan unit moves through a drainage station 30 were the allantoic fluid drains by gravity from an opening in the bottom of the pan and is collected in a drainage trough 188 for further processing.

At an outfeed pan and invert station 32, the tray/pan is re-inverted so that the drain pan is again on top of the tray 36. The pan is then removed from the tray and directed to a rinse unit 33 via rails were the pan is rinsed and processed for reuse at the infeed pan and invert station 28. The egg tray is then inverted over a waste collector, dumping the egg remains into the debris waste system.

Finally, at the tray outfeed station 34, the used trays are transported from the apparatus 20 to a downstream tray washer (not shown) where the trays are processed for re-use. The above described process is a continuous one, with trays proceeding one after the other in a continuous feed through the apparatus.

Having described generally the overall apparatus 20, a more detailed description of the apparatus 20 is now provided.

The eggs containing the viruses to be harvested are carried through the apparatus 20 on trays 36 as illustrated in FIGS. 2 and 2A. Each tray 36 is capable of holding 36 eggs in a 6×6 square matrix of individual egg support sections 38. Each egg support section 38 includes an opening 40 in which the bottom of the egg rests against egg support edges 40a, the opening 40 allowing an egg lifter arm 122 (FIG. 4) to pass through the opening 40 as explained in more detail below with regard to the egg de-cap station 24. Tabs 42 extending upwardly along the sides of the individual egg support sections 38 protect the eggs and keep them from falling from the tray during handling. The tabs 42 should not bind or interfere with the processing of the eggs. Registration projections 44 help align the tray 36 with the drain pan 162 when placed on top of the tray 36 as further described below. Tray posts 44a project downward below the bottom face 44b of the tray 36 and are used to control the movement of the tray as further described. The tray 36 includes notches 46 on two opposing sides as shown which are used to orient the trays in the apparatus 20 as described below. It is understood that other tray configurations may be used, and that the present invention is not limited to the processing of 36 eggs per tray.

With further reference to FIGS. 1 and 1A, at the tray loading station 22, trays 36 with eggs 21 are manually loaded onto the tray loading plate 48 and onto the infeed conveyor 50. The infeed conveyor 50 has rollers 52 positioned on both sides of the apparatus 20 on which the bottom edges of the trays 36 rest. The rollers 52 are rotatably driven to move the trays 36 towards the egg de-cap station 24, and are linked to one another to be driven by a common driver and to ensure that the trays move simultaneously and therefore minimize harsh bumping into one another. The trays 36 are placed onto the infeed conveyor 50 such that the notches 46 in the sides of the trays 36 face one another, and are preferably placed onto the apparatus 20 one after the other to create a continuous feed of trays 36 in contact with one another. The rollers 52 can be powered in any known means such as by motor and chain or gear. Moreover, any suitable tray loading means, manual or automated, and any suitable tray conveyor means may be used. The length of the tray loading station is designed to accommodate the variations of the operators in placing trays into the apparatus 20.

Tray stops 54 hold and release the trays 36 along the infeed conveyor 50 to control the position of the trays 36 in the egg de-cap station 24. As shown in FIG. 1A, the tray stops 54 have a finger 54a that can rotate on shaft 54b between a down position which allows the tray to move forward, and an upward position as shown in FIG. 1A to engage the tray posts 44a (FIG. 2) and stop the forward movement of that tray and all trays behind it. The shaft 54b can be rotated between the two positions by any known means, such as by pneumatic actuators controlled by sensors that detect the trays. In a preferred embodiment, two fingers 54a are provided on each shaft to engage two posts 44a on the under side of the tray 36. It is further understood that additional tray stops 54 are provided as needed to control the flow of trays into and through the egg de-cap station 24, and that each can be independently controlled with use of a tray position sensor to track the position of a tray. The rollers 52 do not stop rotation when the tray stops are activated, but continue to rotate, simply sliding against the bottom of the tray 36.

As seen in FIGS. 1 and 1A, the trays 36 move from the egg tray loading station 22 to the egg de-cap station 24 on the rollers 52 with the forward motion of the trays controlled by the tray stops 54. In the preferred embodiment, at the egg de-cap station 24 there are two separate de-cap units 56a and 56b where the eggs are raised out of the trays 36 for de-capping. One of the de-cap units will cut the even rows of eggs in the tray, the other unit will cut the odd rows of eggs. The cut egg caps are then discarded via a debris removal system and the eggs are lowered back into the trays 36 for further processing. This section of the apparatus 20 is now described in further detail.

With further reference to FIGS. 1, 1A and 3, it is seen that the egg de-cap station 24 includes the first and second de-cap units 56a and 56b positioned above the tray conveyor so that the trays 36 of eggs can move underneath them. Due to tolerances and space requirements, the apparatus of the illustrated embodiment cuts half of the eggs of a given tray 36 in the first de-cap unit 56a and the other half in the second de-cap unit 56b. Additional embodiments, not presently shown, contemplate the use of one or multiple de-cap units (e.g., units 56a, 56b . . . 56n) in any arrangement at the de-cap station 24 depending on the particular embodiment and tray configuration. Alterations of the present invention from the presently illustrated two de-cap units 56a and 56b will require modifications to the apparatus, not presently shown, of one or more of the subassemblies therein (e.g., modifications to the egg lifter arms 122, reference plate 60, de-cap plate 70, and debris wiper plate 88, etc.). With further reference to FIG. 3A, which shows the location of the trays 36a and 36b respectively underneath the first and second de-cap units 56a and 56b, it is seen that the eggs 21 in tray rows R2, R4, and R6 are lifted from the tray for cutting in the first de-cap unit 56a (the eggs lifted from the tray for cutting are not shown); the eggs in rows R1, R3, and R5 are lifted from the tray for cutting in the second de-cap unit 56b. With further reference to FIG. 3G (see the egg 21), it is preferable to cut the upper section 21a of the eggs at the air sac as is known in the art. The eggs 21 are cut and then lowered back into the trays for further processing. In FIG. 3A, the direction of flow for the trays is from right to left, from de-cap unit 56a to unit 56b (arrow 57).

With reference to FIGS. 3 through 3M, the de-cap units 56a and 56b are now described. The two de-cap units are similar in construction and thus only one unit will be described. Exploded views of the de-cap units are shown in FIGS. 3B and 3C. Each of these de-cap units include three main components, a reference plate 60, a de-cap plate 70, and a debris wiper plate 88. The reference plate 60 remains stationary. The de-cap plate 70 and debris wiper plate 88 form a single upper portion unit 102, both of which plates 70, 88 are movable relative to one another and the reference plate 60. The reference plate 60 is described first.

To control where the cut is made on any given egg 21, each egg is referenced, i.e., the section of the egg 21 to be cut (or "de-capped") is fixed. In the illustrated embodiment, the referencing of each egg 21 is carried out with a circular reference opening 58 formed in the reference plate 60. FIG. 3B shows the relationship of the reference plate 60 to the rest of the de-cap unit; FIG. 3C shows an isometric view of the reference plate 60; FIG. 3D shows an enlarged view of the reference opening 58; and FIG. 3E shows a cross-sectional view through the reference plate 60 with an egg positioned within the opening 58.

An egg 21 is lifted upwardly from the underside of the tray 36 as oriented in FIGS. 3B, 3D, and 3E into the reference opening 58 until the egg 21 contacts the opening 58, the opening 58 acting as a stop. A preferred diameter for the reference opening 58 (on the top face of the plate) is about 26 mm to facilitate a cut diameter of the egg of about 21 mm (a range from about 15 to about 35 mm depending on the egg size). It is understood that by changing the diameter of the reference opening 58, the size of the upper section of an egg to be cut can be changed. It is further understood that eggs can vary in size and thus the reference opening 58 is chosen to provide the desired range of cut dimensions for a given range of egg sizes. Put another way, because the sizes of the eggs can vary, the size or configuration of the reference opening 58 allows a predetermined approximate amount of egg (within the desired range) to extend therethrough.

Figure 3A:
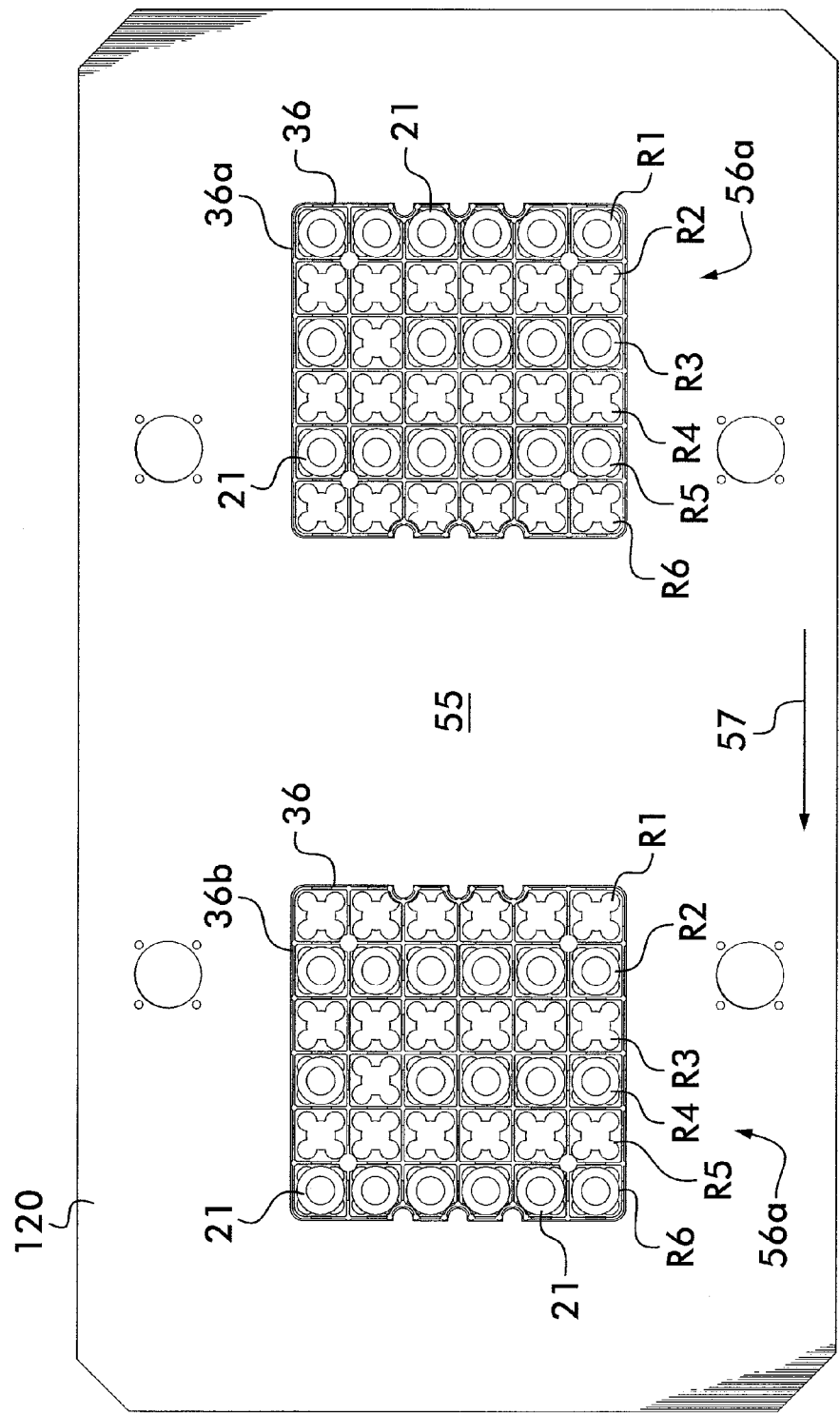
FIG. 3A is a top view of the egg trays in the egg de-cap station illustrating which rows of eggs are cut at which de-cap unit (eggs not shown in the trays were lifted out of the tray for cutting)

Due to the thickness of the reference plate 60, and with particular reference to FIGS. 3D and 3E, the reference opening 58 is formed as an exit opening 58a on the upper plate face 60a, and extends downward through the plate 60 to an inlet opening 58b in the lower plate face 60b (the underside). Inlet opening 58b is sufficiently larger in diameter to account for the curved surface of the egg and to allow the egg to extend fully into the reference opening 58a, the angle through the plate opening 58a to opening 58b is preferably in the range from about 45° to about 120°, and more preferably about 70° as shown. With reference to FIG. 3E, it is appreciated that the cap of the egg to be cut extends upwardly from the reference opening 58 for cutting. Each of the two reference plates 60 have 18 reference openings 58 arranged in three rows corresponding to the rows shown in FIG. 3A, i.e., one reference plate 60 for de-cap unit 56a has the reference openings arranged to cut the eggs in three rows—R2, R4 and R6 of tray 36a (FIG. 3A); the other reference plate for de-cap unit 52b has the openings arranged to cut in rows R1, R3 and R5 of tray 36b. Thus, in the present embodiment, half of the eggs of a tray are cut at one de-cap unit, the other half at the other de-cap unit.

The upper face 60a of the reference plate 60 includes linearly extending channels 62 on either side of the reference openings 58 (see FIGS. 3C and 3D). With specific reference to FIGS. 3C, 3D and 3E, the reference plate 60 further includes debris removal openings 64. For each reference plate 60, there are 18 circular debris removal openings 64, one such opening 64 positioned adjacent to each of the 18 reference openings 58 as shown. The debris removal openings 64 open to an angled channel 66 extending between the reference opening 58 and the debris removal opening 64 associated therewith. It is seen that each angled channel 66 slopes downward towards the debris removal opening 64 to facilitate removal of the debris created by the egg de-capping. Finally, it is appreciated that the reference plate 60 can be made of any suitable material for pharmaceutical use, such as stainless steel.

Figure 3F:
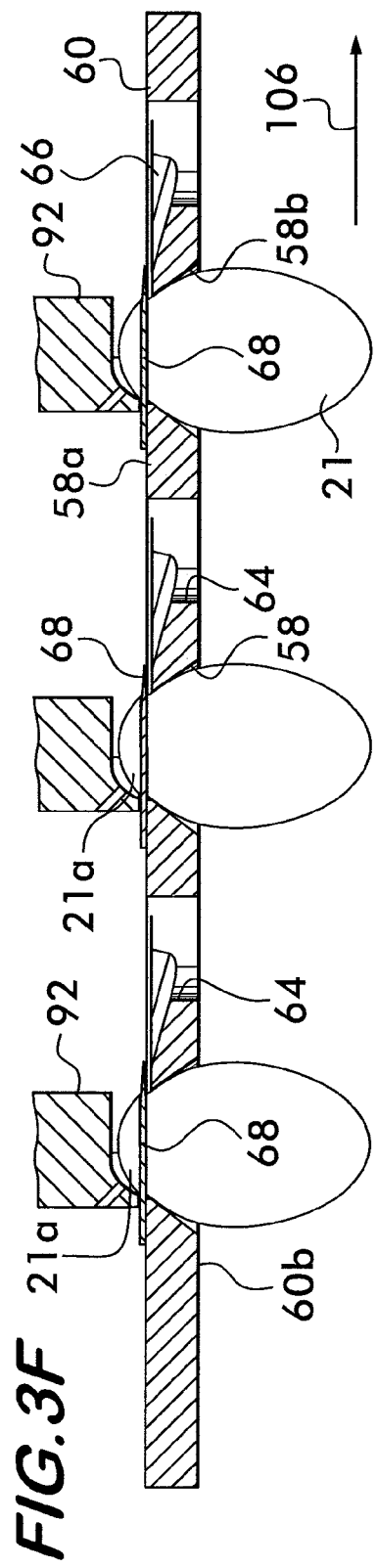
FIG. 3F is the same as FIG. 3E, but illustrating the position of the cutting blades, wiper caps, and eggs relative to the reference plate during the process of cutting the eggs.
Figure 3G:
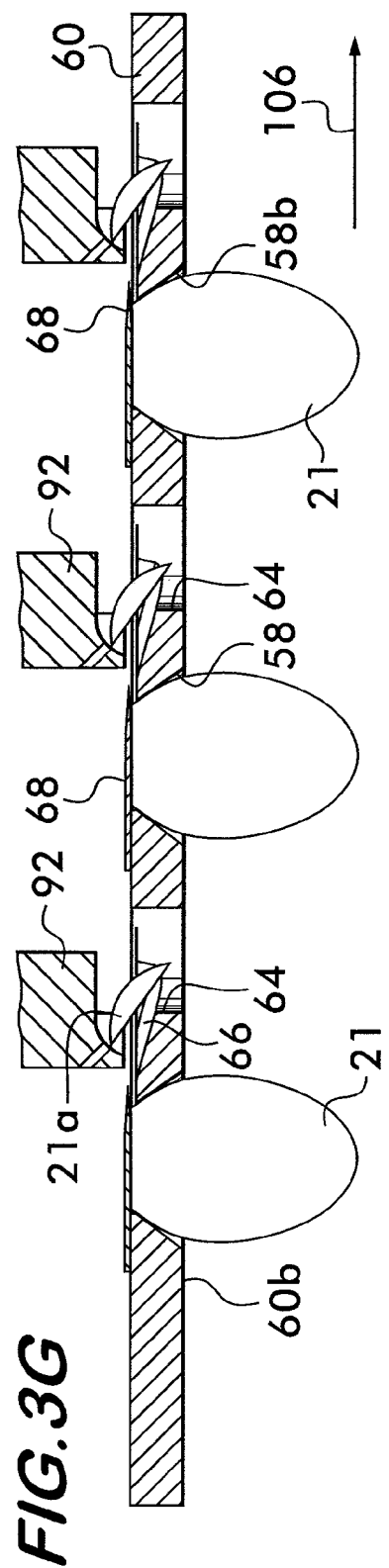
FIG. 3G is the same as FIG. 3E, but illustrating the position of the cutting blades, wiper caps, and eggs relative to the reference plate after cutting the eggs and during the process of removing the cut egg cups.
Figure 3I:
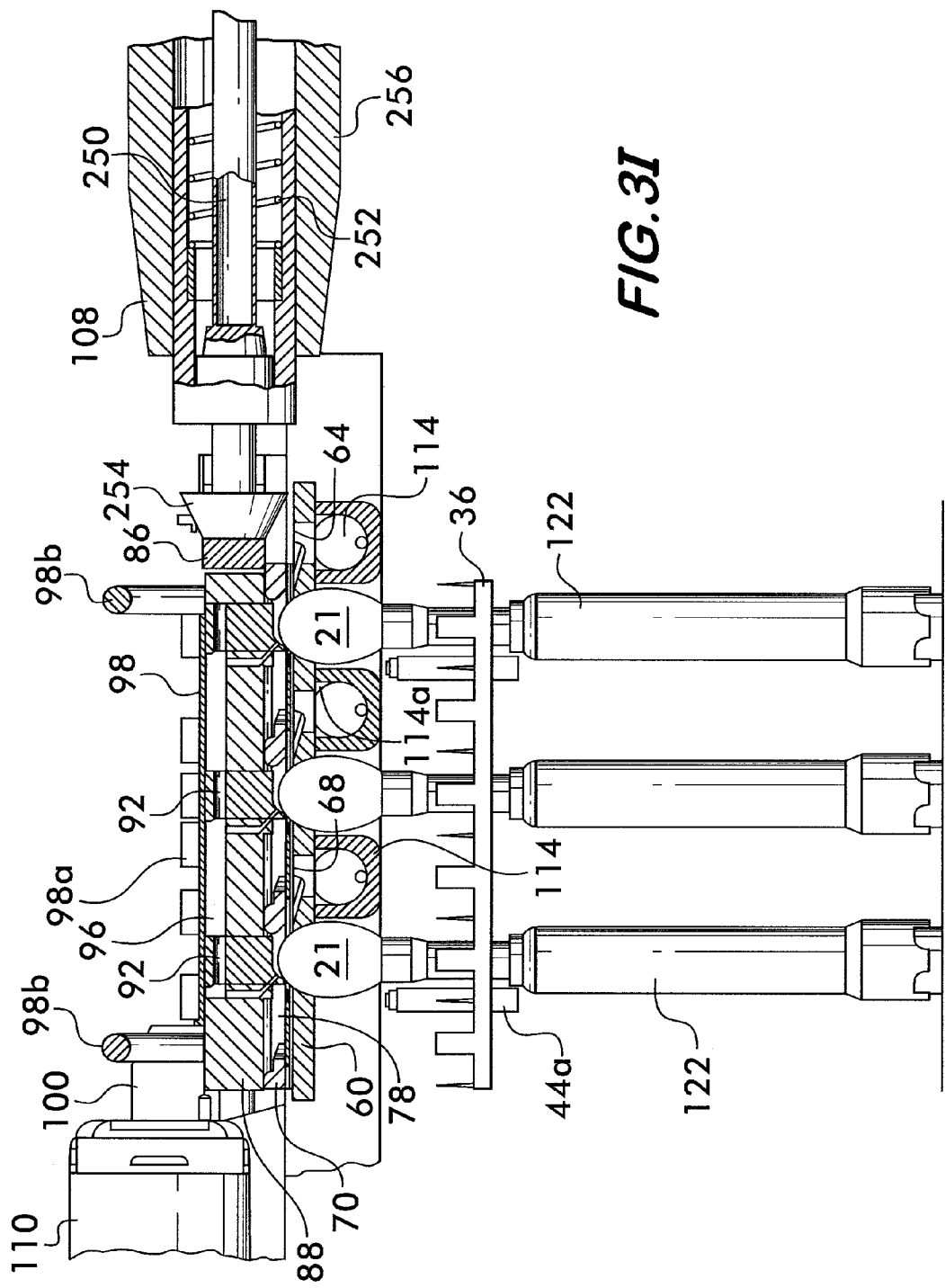
FIG. 3I is a cross sectional view of the reference plate, de-capping plate and debris wiper plate taken along line 3I-3I in FIG. 3 and showing three eggs lifted into the reference plate openings prior to the cutting of the egg caps.

The de-cap plate 70 forms a cutting member positioned directly above the reference plate 60 for cutting the eggs 21 (see FIGS. 3B, 3C and 3I, the de-cap plate 70 being part of the upper portion 102 positioned above the reference plate 60 as shown in FIG. 3C). With further reference to FIG. 3H, the de-cap plate 70 includes 18 cutting members 68 which, in the preferred embodiment, are provided in the form of cutting blades 68, one for each reference opening 58. The blades 68 are attached to the underside of the de-cap plate 70 via blade retainers 72 which have registration protrusions 74 for mating with blade notches 76 to properly align the blades with the reference openings 58 of reference plate 60 (FIG. 3E). With reference to FIG. 3H, the blades 68 preferably have a thickness in the range from about 0.5 to about 2.5 mm, and more preferably about 1 mm in thickness, and made from a stainless steel material suitable for pharmaceutical use. The cutting edge of the blade is preferably formed of two sharp edges 69 extending back at about a 20° angle from the front center point of the blade, although other angles, such those within the range from about 0° to about 60° may be acceptable. Other suitable blade configurations and angles are possible, as are blades with one, two, and three or more edges positioned at various angles from the center or another point on the blade. In still other embodiments, blades are provided having concave, convex, and/or serrated edges. The blade retainers 72 are held to the underside of the de-cap plate 70 with screws 77 and screw holes 79 (FIG. 3C).

Eighteen generally rectangular openings 78 are formed in the de-cap plate 70, each opening 78 being configured to align above and cooperate with the one of the reference openings 58 and the debris removal opening 64 associated therewith of the reference plate 60 as further described below. It will further be seen that the openings 78 are sized and configured to permit a wiper cap 92 of the wiper plate 88 to move back and forth therein as further described below. Put another way, during the egg cutting process, the de-cap plate 70 moves back and forth relative to the reference plate 60 to cut the eggs. This motion carries the blades 68 across the reference opening 58 and then back again (see FIGS. 3E, 3F, and 3G illustrating the movement of the blades 68 over a reference opening 58 to cut the eggs 21). Since the openings 78 of the de-cap plate moves with the blades 68, the openings 78 of the de-cap plate must be sized for the relative movements of the wiper cap 92 therein as is further described below. Preferably, with reference to FIG. 3C, the rows of blades 68 are offset by about 0, 3, and 6 mm from one another so that the three rows of blades, e.g. rows R2, R4, R6, do not contact the eggs at the same time. Other suitable offset dimensions can be used e.g., offsets from about 0 to about 9 mm.

With further reference to FIGS. 3B, 3C and 3D, to ensure proper alignment, the blade retainers 72 of the de-cap plate 70 extend into and are slidable within the channels 62 of the reference plate 60. Rod guides 80, attached to the de-cap plate 70, engageably slide over stationary rods 82 (FIG. 3C). The rods 82 are held stationary by rod holders 83 (FIG. 3). An actuator coupling 86, attached by screws to the de-cap plate 70, which attaches to an actuating arm as described below, moves the de-cap plate 70 back and forth between the precut and post cut positions. The motion and stroke of the de-cap plate 70 is controlled by the actuator 108 as described below. The clearance between the de-cap plate 70 and the reference plate 60 is preferably from about 0 to about 5 mm, with about 1.5 mm being more preferred, and the clearance between the blades 68 and the reference plate is preferably about 0.5 mm. The blade stroke over the reference opening 58 is preferably from about 25 mm to about 60 mm, and more preferably at least about 40 mm. While preferred for the present embodiment, other suitable dimensions and tolerances may be used.

With reference to FIG. 3C, the debris wiper plate 88 is positioned above the de-cap plate 70 and includes rod guides 90 slidable on the rods 82 as controlled by the actuators 108 and 110. Cleaning members 92 for removing the debris created by the cutting process, in the form of debris removal caps 92 as shown in the preferred embodiment, are supported on the wiper plate top face 88a by cap top 92a. The caps 92 are mounted in and extend through openings 94 in the wiper plate 88 and extend downward through the openings 78 of the de-cap plate 70 to be positionable over an associated reference opening 58. The clearance between the blades 68 and the debris removal caps is preferably less than about 0.25 mm, and more preferably about 0.127 mm or less.

With further reference to FIG. 3L, the bottom end of the debris removal caps 92 has a partially spherically shaped face 92b configured for receiving the top cap of the egg 21, and which ends in a semi-circular edge 92c. An air outlet opening 92d, receiving air from air inlet 92e, is positioned to blow air into the concave area formed by the spherically shaped face 92b. Air channels 96 are formed in the debris wiper plate 88 (FIG. 3C) for delivering air from an air source to the debris removal caps 92. As an alternative, air may be delivered to the opening 92d from an opening in the back side of the cap 92 opposite of the opening 92d, such as from an air conduit as shown in FIG. 3I. A cover plate 98, cover screws 98a, handles 98b, and actuator coupling 100 complete the upper portions 102 of the de-cap units 56a and 56b, which sit above the reference plates 60. See FIGS. 3B and 3C. The blade set up plates 104 shown in FIG. 3B are used for set up purposes and do not form part of the working embodiment. The motion and stroke of the debris removal plate 88 is controlled by the actuator 110.

Figure 3J:
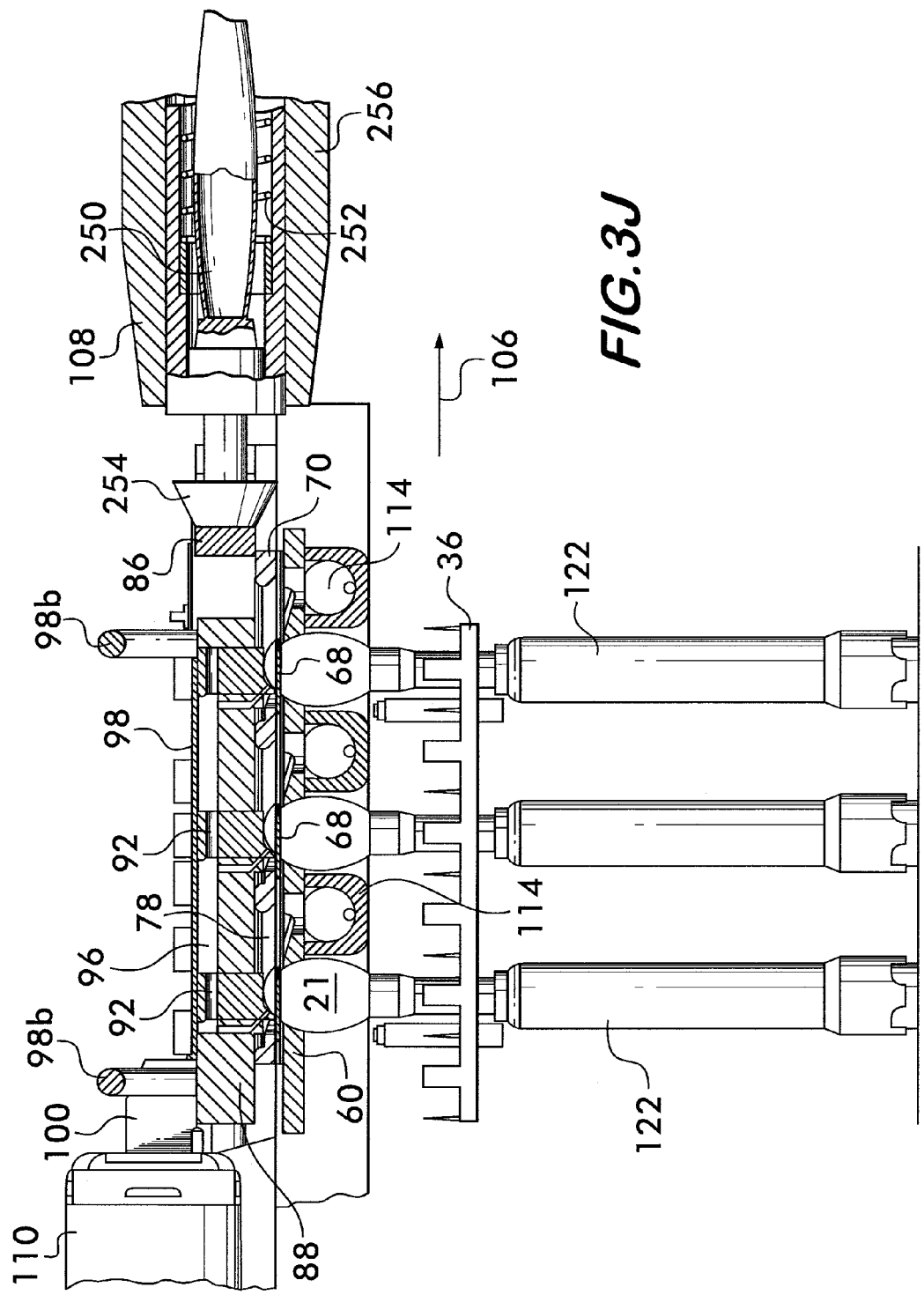
FIG. 3J is a similar view to that if FIG. 3I, but showing the reference plate, de-capping plate and debris wiper plate during the cutting of the egg caps.

The movements of the de-cap and debris wiper plates 70, 88 relative to the reference plate 60 for de-capping the eggs 21 are now described with reference to FIGS. 3, 3B, 3C, and 3D, and particularly to FIGS. 3E, 3F, 3G, 3H, 3I, 3J and 3K. FIGS. 3E, 3F, and 3G are cross sectional views of the reference plate 60 illustrating the movements of the de-cap blades 68 and the wiper caps 92 and showing eggs in the reference openings 58. FIGS. 3H, 3I, and 3J are similar to FIGS. 3E, 3F, and 3G, but showing more structure and details, and are cross sectional views of the reference plate 60, de-capping plate 70 and debris wiper plate 88 showing three eggs lifted into the reference plate openings 58. As seen, lifting arms 122 (which are further described below) have lifted the eggs 21 from the tray 36 into the openings 58 of the reference plate 60. With specific reference to FIGS. 3E and 3I, which shows the plates and eggs in the pre-cut position, it is seen that the de-cap plate 70 is positioned such that the blades 68 are adjacent to the reference openings 58 of the reference plate 60, i.e., the blades 68 are to the left of the eggs 21 as oriented in FIGS. 3E and 3I. It is further seen that in the precut position the wiper plate 88 is also to the left positioned so that the removal caps 92 sit over the reference openings 58 such that the eggs 21 are within the spherically shaped cap faces 92b. For purposes of orientation, this view is consistent with the de-cap station 56a in FIGS. 3 and 3B, i.e., the de-cap and wiper plates 70 and 88 are in the left most position relative to the reference plate 60. The direction of the movements for the second de-cap station 56b is reversed from that being now described. The reference plate 60 remains stationary while the de-cap plate 70 and wiper plate 88 move to carry out the de-cap process in various steps as now described.

In a first movement, with further reference to FIGS. 3F and 3J, and with the reference plate 60 and wiper plate 88 remaining stationary, the actuator 108 pulls the de-cap plate 70 in the direction of the arrow 106 (rightwardly for de-cap station 56a as illustrated in FIG. 3B), pulling the blades 68 through the eggs 21 to a post cut position where the blades 68 now cover the reference openings 58 and are positioned between the reference openings 58 and the removal caps 92 of the wiper plate 88, the cut egg sections 21a being shown detached from the eggs and above the blades 68.

In a second movement, with further reference to FIGS. 3G and 3K another actuator 110 then pushes the debris wiper plate 88 in the direction of the arrows 106, moving the debris removal caps 92 over the debris removal openings 64 in the reference plate 60 below it, thereby pushing the shell debris 21a down the angled channels 66 into the removal openings 64. At the completion of this second movement, both the de-cap plate 70 and the debris wiper plate 88 are in the post cut position, both plates 70, 88 have moved to the right relative to the reference plate 60 as oriented in FIG. 3J.

Figure 3K:
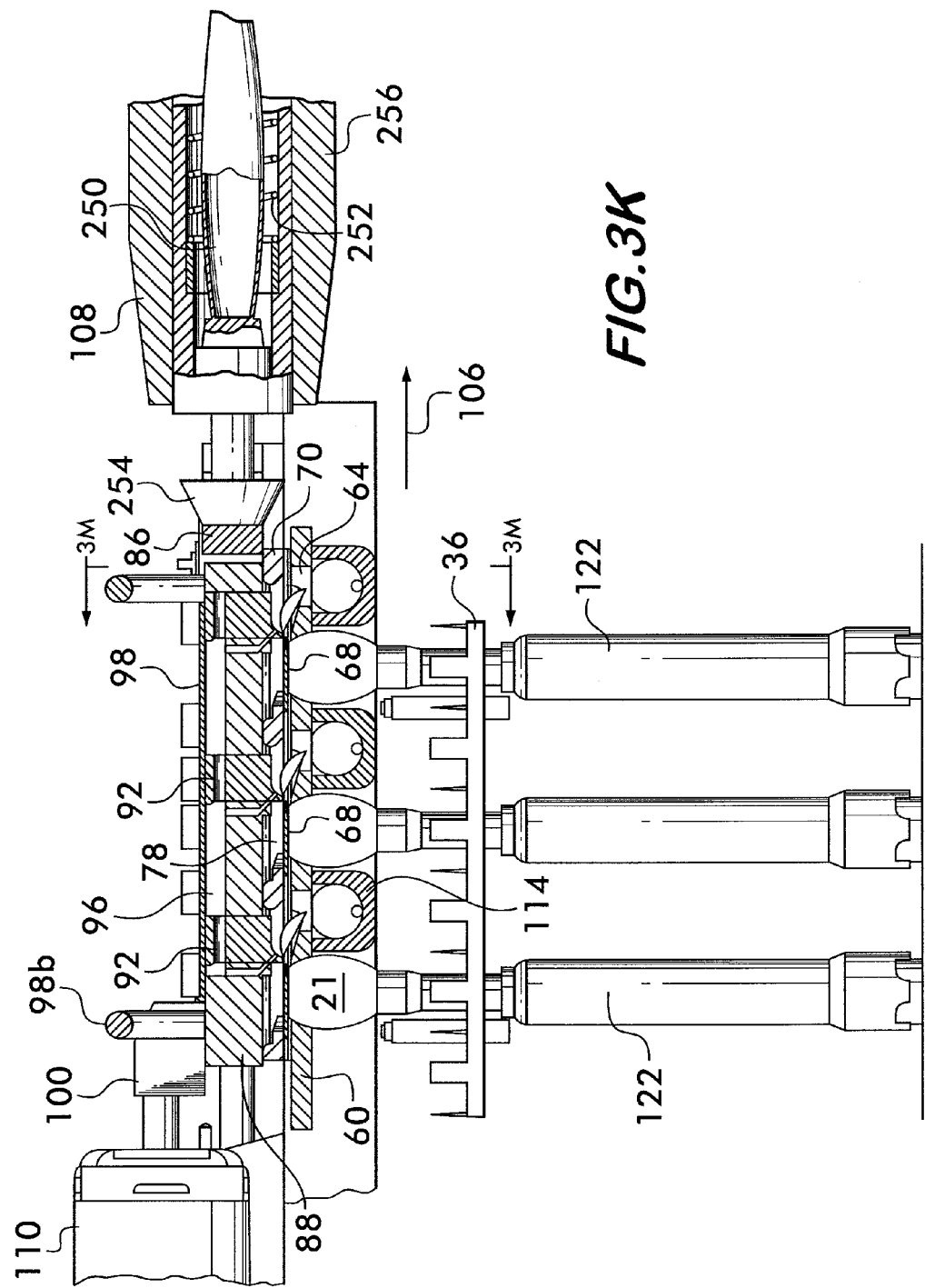
FIG. 3K is a similar view to that if FIG. 3I, but showing the reference plate, de-capping plate and debris wiper after the cutting the egg caps and during the process of removing the cut section of the eggs.
Figure 3N:
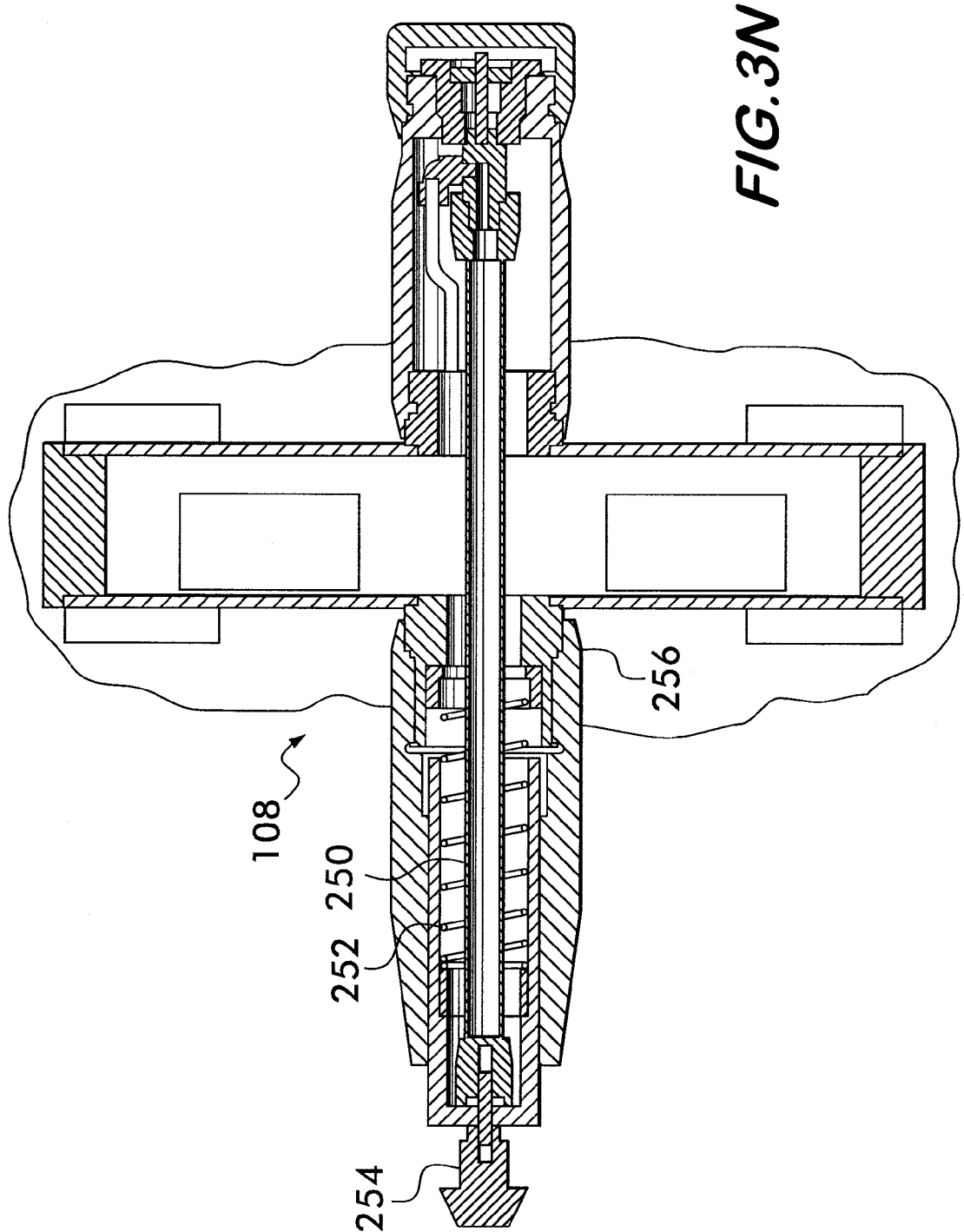
FIG. 3N is a cross sectional view of an actuator having a fluidic muscle.

In a third movement, the actuator 110 pulls the wiper plate 88 back to the precut position, opposite direction of arrow 106 in FIGS. 3G and 3K and going back to the position shown in FIGS. 3F and 3J.

In a fourth and final movement, the actuator 108 that pulled the de-cap plate 70 in the first movement now pushes the de-cap plate 70 back to the precut position (opposite direction of arrow 106 and going back to the position shown in FIGS. 3E and 3I) for cutting the next group of eggs 21. It is appreciated that the openings 78 of the de-cap plate 78 must be sized to accommodate the relative movements of the wiper caps 92 back and forth within the openings 78 as the de-cap plate 70 moves relative to the reference plate and wiper plate to cut the egg in the first step (the cap 92 moving to an opposite side of the opening) and then as the cap 92 of the wiper plate 88 moves relative to the reference plate and wiper plate to wipe away the cap debris in the second step (the cap 92 moving back to the side of the opening 78 that it started in prior to the first step).

Put another way, and again with specific reference to FIGS. 3E, 3F, 3G, 3I, 3J, and 3K, in the first movement, the de-cap plate 70 with blades 68 of the de-cap unit 56a on the right side of FIG. 3B is pulled to the right (arrow 106) by actuator 108 acting on coupling 86 to de-cap the eggs. In the second movement, the debris wiper plate 88 with wiper caps 92 is pushed to the right (arrow 106) by actuator 110 acting on coupling 100 to push the debris into the debris removal openings 64 of the reference plate 60. In the third movement, the debris wiper plate 88 is pulled to the left (opposite arrow 106) by the actuator 110 to return it to its precut position. In the fourth and final movement, the de-cap plate 70 is pushed back to the left (opposite arrow 106) by actuator 108, acting on coupling 86, moving back to the precut position over the stationary reference plate 60. While the present embodiment has the above described sequence of movements, it is understood that this sequence may be modified or altered as suitable for other embodiments of the invention. For example, the de-cap plate 70 and wiper plate 88 could be returned to there pre-cut positions together by one of the actuators in a single step rather than separate steps, e.g., the de-cap plate could be configured to pull the wiper plate with it when moving back to its pre-cut position.

The actuators 108 and 110 can be of any suitable type mechanism. For example, in the preferred embodiment, with reference to FIGS. 3 and 3N, the actuator 108 of the present embodiment is formed from a longitudinally cylindrical fluidic muscle 250 which, when pressurized with a gas, such as air, expands diametrically and thereby contracts longitudinally against the force of a spring 252 to pull the joint 254 and thereby pull coupling 86. When the air pressure is released from the fluidic muscle 250, the spring 252 returns the muscle to its original configuration and length, thereby pushing the coupling 86. The fluidic muscle and spring are contained within a stainless steel housing 256 and supplied with a compressed gas as is known in the art. A suitable supplier of fluidic muscles is Festo AG & Co. KG. Nevertheless, any suitable actuating mechanism may be used in place of or in addition to a fluidic muscle. The actuator 110 can be an air cylinder type actuator, among others.

With further reference to FIG. 3 and particularly FIG. 3B, the reference plate 60 is mounted on support members 112 with clamps 112a. Debris removal channels 114 have openings 114a positioned below the debris removal openings 64 to collect the debris. Timed blasts of compressed gas, such as air, can be used for dry removal of the debris through the channels 114 to waste collection conduits 116 (see FIG. 1A). FIG. 3M, taken along line 3M-3M of FIG. 3k, shows the relationship of the reference plate 60, de-cap plate 70 and wiper plate 88 from another angle.

The process by which the eggs 21 are lifted out of the tray 36 and up against the reference plate 60 is now described with reference to FIGS. 1A, 3A, 4, and 4A. FIG. 3A is a top view looking down on the egg trays 36 from beneath the de-cap units. FIG. 4 is an isometric view of the egg lifting assembly and FIG. 4A is a side view of the egg lifting assembly with the side of the table removed to show the inner elements. For orientation purposes, positioned within a processing table 118 (FIG. 1A) below the de-cap units 56a, 56b is an enclosure 120 housing the equipment used to lift the eggs 21 from the trays 36 up into the reference plate 60 (FIG. 4). The housing has a top 120a and a bottom 120b that rests on the floor. Each de-cap unit 56a, 56b cooperates with one of the sets of 18 cylindrical egg lifter arms 122 to lift eggs 21 up from the tray 36 to the reference plate 60. The lifter arms 122 are sized to fit within the openings 40 of the tray 36. As can best be seen in FIG. 4A, all 36 lifter arms 122 (18 arms for de-cap unit 56a, and 18 arms for de-cap unit 56b) move up and down in unison with a servo plate 124 controlled by servo motor 124a via shaft 124b. The servo plate 124 moves two nest blocks 126 via connector rods 128, each nest block 126 moving 18 of the arms 122. A drive shaft 130 for each of the arms 122 is connected to one of the nest blocks 126 through a compression spring 132 (FIG. 4B) that compensates for the variability in egg sizes, i.e., a larger egg may contact the reference plate 60 before a smaller egg and thus the spring 132 would take up the additional distance that the servo plate 124 would move to bring the smaller egg up against the reference plate 60. The drive shafts 130 extend through the enclosure top 120a and preferably include a vibration isolation mount 130a.

In the illustrated embodiment, the drive shafts 130 are not physically connected to the lifter arms 122, but are magnetically coupled to one another to move in unison therewith. As seen in FIGS. 4A and 4C, each drive shaft 130 moves up and down within a stationary or static cylindrical coupler tube 138 that is threadingly fixed to the enclosure top 120a via a threaded coupling 120c and which has a cap 138a to seal closed the top of the coupler tube 138. The lifter arm 122, coaxial with the drive shaft 130 and coupler tube 138, moves slidably up and down over the coupler tube 138 in unison with the drive shaft 132 to which it is magnetically coupled.

With further reference to FIGS. 4A, 4B, 4C, 4D, 4E, and 4F, drive shaft 130 extends through the enclosure top 120a through the circular threaded collar 120c attached to the enclosure 120a, and includes a cylindrical coupler piston 134 moveable up and down above the enclosure top 120a within the coupler tube 138 (see FIGS. 4B and 4C). The coupler piston 134 has an alignment cap 136 screwed thereto which is slightly larger in diameter than the diameter of the coupler piston 134. Four columns (eight rows) of magnets MC-1 through MC-16 are attached to the coupler piston 134 a shown.

The lifter arm 122 includes a cylindrical hollow sleeve portion 140, a cylindrical drip shield 142, a cylindrical extension sleeve 140a, and an egg cup 144 (FIG. 4C, 4F). The egg cup 144 preferably has four arms 144a as shown in FIG. 4F configured to receive and hold the egg 21, although other suitable configurations, e.g., more or less arms, may be used. The egg cup 144 is preferably made of a polymer material within the range of about 30 to about 90 Shore A durometer polyurethane, and more preferably 65 Shore A durometer polyurethane, and is sized to fit through the openings 40 of the egg trays 36. Attached to the inside of the cylindrical hollow sleeve 140 is a coupler magnet cartridge 146 which contains four columns (eight rows) of magnets ML-1 through ML-16 which align with complementary magnets MC-1 through MC-16 of the coupler piston 134. The upper row of magnets may be thinner than those of the other rows to allow for the screw 136.

The magnetic forces between the magnets (MC-1 through MC-16) of the coupler piston 134 and those (ML-1 through ML-16) of the lifter arm 122 couples the two together such that the lifter arm 122 moves with the coupler piston 134. This configuration advantageously provides a sealed connection between the lifter arm 122 in the coupler piston 134 to prevent debris or contamination from passing between the two, and makes it easier to clean. Other configurations and designs are contemplated, such as direct connections from the actuator to the lifting arms.

In operation, the eggs are lifted preferably from the tray 36 in a manner to adjust the alignment of any of the eggs that may be out of alignment. As noted previously, it is desirable to cut the top section of the egg 21 in the air space. The handling of the eggs and the trays may cause some of the eggs to move out of alignment. In the preferred embodiment, to align the eggs prior to cutting, the lifter arms 122 first lifts the eggs 21 a short distance above the tray 36 and then quickly reverses direction to unweight the eggs 21 sufficiently such that the eggs realign under the action of gravity. The lifter arms 122 then carry the eggs 21 all the way to the reference plate 60 where the eggs are referenced and de-capped. An egg lift brake is provided to lock the lifting arms in place so that they cannot move during the cutting process. This stops the eggs from lowering as the blades make the cut, and can be provided in any suitable manner, such as by braking the nest blocks 128. Although the above described method of lifting eggs is preferred for the present embodiment, other suitable means for bringing the eggs into contact with the reference plate may be used. For example, to re-align the eggs, sequences of motion other than the two movements (up and then quickly down) are contemplated.

In summary, and with reference to FIG. 1A, a tray 36 containing thirty-six eggs 21 is supported on and conveyed forward towards the de-capping station by the rollers 52. The tray stop 54 releases the tray 36 which is then conveyed by rollers 52 into the first the de-capping unit 56a where another tray stop 54 stops further movement of the tray. Stationary tray hold down bars (not shown) are positioned just above the tray 36 in the de-capping units to prevent upward movement of the tray. The lifting arms 122 then lift eighteen eggs from the tray and quickly reverse direction to better align any misaligned eggs. The lifting arms 122 then lift the eighteen eggs all the way up to the referencing plate 60 and, while the eggs are held against the reference plate 60 with the lifting arms 122 locked in position, the de-cap plate 70 is pulled to the right (arrow 106) as oriented in FIG. 3 to remove the egg caps. Next the debris wiper plate 88 is pushed to the right to move that the debris into the debris removal openings 64. Next, the debris wipe plate 88 is pulled back to the left (opposite of arrow 106) to the precut position, followed by the de-cap plate 70 pushed back to the left (opposite of arrow 106) to the precut position. The lifter arms 122 return the de-capped eggs to the tray 36, which tray is then released by the tray stops 54 to be conveyed by the rollers 52 to the intermediate position 55 between the two de-capping units 56a, 56b (see FIG. 3A) where the tray is held by another tray stop 54 while a second de-capping process is carried out in the two de-capping units 56a, 56b on the trays immediately behind and immediately in front of the present tray. Upon completion of this second de-capping process, the tray is again released and stopped at the second de-capping unit 56b by another tray stop 54. A third de-capping process is carried out to de-cap the remaining 18 eggs in de-cap unit 56b, the tray 36 immediately behind the present tray now being held at the intermediate position 55. The eggs cut in the first de-capping unit 56a remain covered under the reference plate while in the second de-capping unit 56b to prevent debris from falling in. This process is carried out in a continuous manner with a tray 36 moving to the de-capping unit 56a, then the intermediate position 55, and then the second de-capping unit 56b.

With all eggs in the tray 36 now de-capped, the tray is released and conveyed on the rollers 52 towards the inspection station 26. With reference to FIGS. 5 and 1A, once outside the de-capping station 24, an indexing tray pusher 150, using two indexing arms 152 having tray pusher fingers 154 that move linearly back and forth and rotate upward to engage the tray posts 44*a*, pushes the tray on two slide rails 156 one index position (the length of a tray), repeating this process for each tray coming from the de-cap station, and thereby moving all trays in contact therewith forward in unison through the inspection station 26. The rails 156 can include a ledge to keep the trays thereon. The rollers 52 do not extend into this area and thus no longer convey the trays from this point forward.

With reference to FIGS. 1 and 1A, at the inspection station 26 the de-capped eggs are manually inspected. In the illustrated embodiment, the inspection station provides for two operators, one on either side of the apparatus 20, to manually inspect each egg, and reach the eggs through oval gloveless ports as shown, although glove or sleeve ports can be used. Each operator has room within the enclosure for an empty tray 36 to store unde-capped eggs for reprocessing once the tray is filled. Rejected eggs can be discarded into a waste port 148 at each inspection station. The egg trays continue through the inspection station 26 to the end of the rails 156 at the infeed pan and invert station 28 (FIGS. 1, 1A, 1B, 6, 6A and 6B). It is preferable to provide an atmospheric pressure in the area of the invert station 28 and downstream thereof that is higher than the pressure in the inspection and preceding areas. In this way, as is known in the art, the air flows from the higher pressure zone to the lower, preventing any dust and other debris from reaching the higher pressure areas where the allantoic fluid is exposed.

Figure 6B:
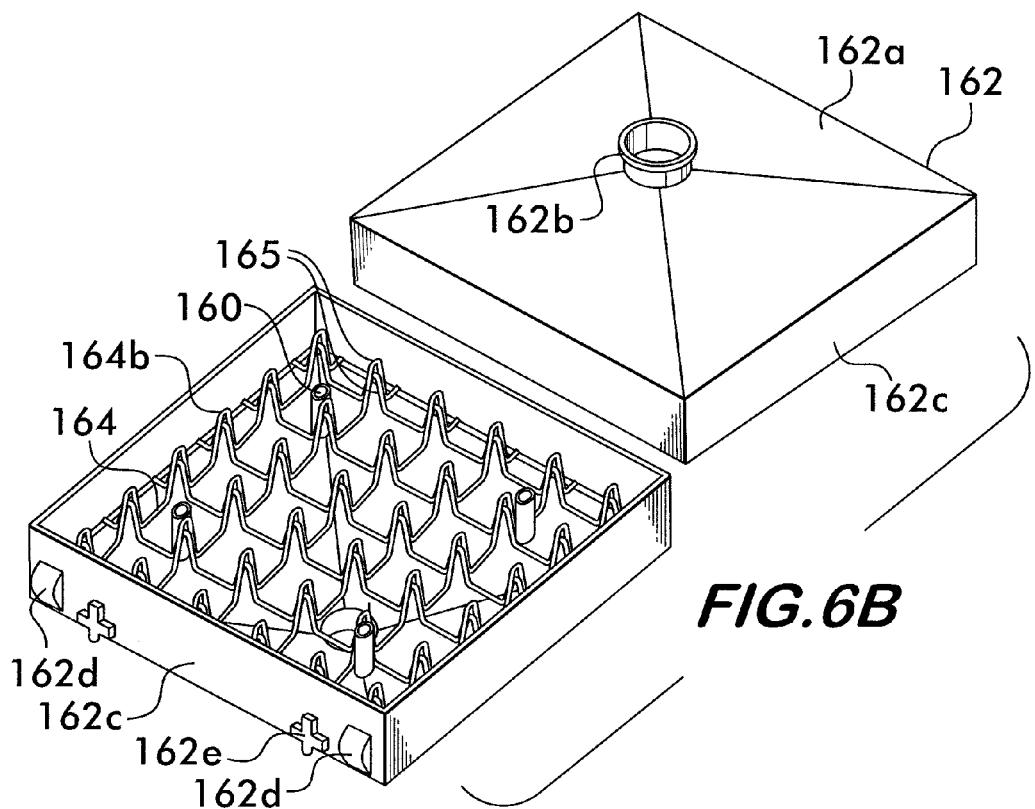
FIG. 6B an isometric view of two drain pans, the right pan showing the top and the left pan showing the bottom.

At the infeed pan and invert station 28, the tray 36 is mated with a drain pan 162 and inverted (turned upside down) to drain the allantoic fluid. See FIGS. 6, 6A and 6B. With reference to FIG. 6B, showing one pan in a non-inverted position (on the right) and another in an inverted position (on the left), the drain pan 162 is rectangular in shape and configured to fit over the tray 36. It has a pan top 162*a* having a flared central drain spout 162*b*, and pan sides 162*c*. The drain spout 162*b* is preferably not positioned to be directly below the opening of an egg when mated with a tray 36 so that the allantoic fluid does not fall from the egg directly into the drain spout as the added distance of the fall could cause the allantoic fluid to foam. One of the pan sides includes two pan bumpers 162*d* to space the adjacent pans from one another on the rails and pan screws 162*e* to hold an embryo retainer 164 to the pan and allow removal for cleaning. Registration slots 160 attached to and extending from the underside of the top of the pan receive the registration projections 44 of the tray 36 for proper alignment of the pan on the tray.

The retainer 164, attached to the sides of the pan, forms retainer members 164*b*. In the preferred embodiment, the retainer members 164*b* take the form of retainer fingers 164*b* where two interwoven retainer forming wire loops 165 intersect, the wires having a preferred diameter from about 2 mm to about 6 mm, and more preferably about 3.5 mm, and the height of the outer wire is preferably from about 30 mm to about 50 mm and more preferably about 38.18 mm from the outer diameters of the wires. The fingers 164*b* are configured to extend into the openings of the de-capped eggs 21 to hold the contents of the egg (e.g., the embryo) within while the allantoic fluid drains when the tray is inverted. It is believed that the upper wire of the finger 164*b* ruptures the allantoic membrane to release the fluid while the two wire loops of a finger 164*b* of the fingers provide sufficient surface area to hold the embryo in place without perforating the embryonic membrane, although one wire loop may also be suitable. It is appreciated that the egg shell rests on the wires at the end of the loops, i.e., the flat portion of the wire, and thus the width of the base of the loops must be smaller than the cut diameter of the egg shell. Thirty-six such fingers are provided, positioned to fit into the opening of each egg 21 in the tray. Other finger configurations may be suitable, including those that do not use wire.

The drain pans 162 are provided from the tray rinse unit 33 (FIGS. 1 and 1B) where the pans are rinsed and delivered to the infeed pan and invert station 28 on slide rails in any know manner. Rinsed drain pans 162 are delivered to the pan pick up station 166 (FIG. 6) by any suitable conveyor means and with a final movement by the arm 168 which swings to engage the drain spout 162*b* and push the pan against a stop to accurately position the pan for pick up. A pick and place servo 170 having servo fingers 170*a* grabs the pan 162 by its flared drain spout 162*b* (FIG. 6B), lifts the pan up, rotates the pan over a tray 36, lowers the pan onto the tray, and then opens the fingers to release the pan. The servo 170 is configured to have a high velocity when the pan is not in contact with the eggs, and to decrease velocity for a more gentle and smooth motion when in contact with the eggs. The fingers 170*a* have grip pads to avoid damaging the pans. The pick and place servo 170 preferably has two sets of servo fingers 170*a* on opposite sides from one another (the front side shown in FIG. 6), and rotates in both directions, e.g., with reference to FIG. 6, the pick and place servo 170 first moves clockwise using a first set of fingers 170*a* and is lowered to deliver a pan 162 to a tray while at the same time the fingers 170*a* on the opposite side picks up the next pan at the pick up station 166 to be delivered to a tray by counterclockwise direction. This switching of directions is continued.

The trays are moved into the exact position (pan place position 174) for receiving the drain pan 162 by an index servo 172 (FIG. 6B) having an arm 172*a* and posts 172*b* attached to the arm that pulls the tray 32 (via tray posts 44*a*) along the rails from the end of the inspection station to the pan place position 174. Hold down members 176 attached to the top of the rails above the trays restrict movement of the egg tray when loading a pan onto a tray. Sensors 179 (FIG. 6), e.g. laser sensors connected to a controller, monitor the exact position of the tray, the left sensor controls the position of the tray when the pan is placed, the right sensor is not for pan placement, but to ensure that the tray/pan combination 178 has been moved to the next position and to allow the next pan to be lowered onto the next tray. Once the tray is properly positioned, a drain pan 162 is placed thereon by the pick and place servo 170, with the bumper pads 162*d* orientated so as to contact the adjacent pan as the pan moves through the process.

Figure 6C:
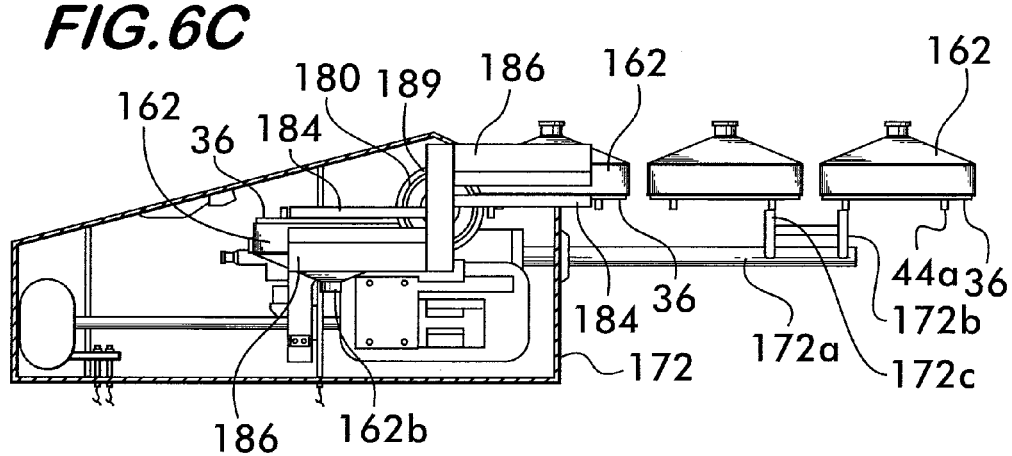
FIG. 6C a side view of the invert unit and tray index servo shown removed from the infeed pan and invert station.

Next the combined tray/pan unit 36/162 (also referenced as numeral 178) is moved to an invert unit 180 by a post 172*c* off of the same arm 172*a* of the same index servo 172 that moved the tray into the pan place position 174. It is seen that the index server 172 moves 2 trays at the same time, one into the pan place position 174, the second (tray/pan) to the inverter member 180. Guide rails 182 support the trays and tray/pan in this area. With further reference to FIGS. 6A and 6C the inverter member 180 receives the tray/pan 178 via the index servo 172 on rails 182. The inverter member 180 has a pair of static rails for holding the tray/pan 178 in place between them during the inversion process; lower static rails 184 made of stainless steel and upper static rails 186 formed of a polymer material such as UHMW. Two sets of static rails pairs 184, 186 are provided on opposite sides of a central shaft 189 that is connected to a rotary servo motor for rotating the invert unit 180. A rod (not shown) in between the two rails 184 positioned to be on the underside of the tray/pan 178 can be provided connected to the rotary servo motor to help hold the tray/pan 178 in place during the inversion process. It is further seen that the rails 182 extend past and in between the front end of static rails 184 of the invert unit 180 so that the tray/pan 178 can slide into the invert unit 180 and allow the invert unit to rotate without interference from the rails 182. Once within the inverter static rails 184, 186, the tray/pan 178 is inverted, moving clockwise as oriented in FIG. 6 (or counter clockwise as in FIG. 6C) to a lower elevation, positioning the tray/pan 178 in an inverted position for draining with the pan drain 162b facing downward, while placing the second set of static rails 184, 186 in position for receiving the next tray/pan assembly 178 to be inverted.

The inversion places the tray/pan assemblies 178 in the drainage station 30 where the allantoic fluid drains from the eggs. Here, the tray/pans 178 are moved over a collection trough 188 from left to right in the drainage station 30 (FIGS. 1 and 1B) during the collection process. With the embryos held within the eggs by retainer fingers 164b (FIG. 6B), and the tray 36 held in the pan 162 by gravity, the allantoic fluid drains from the openings in the eggs into the pans and out of the pan drain spout 162b into the collection trough 188. The tray/pans 178 move slidably above the trough 188 on guide rails 190.

Figure 7:
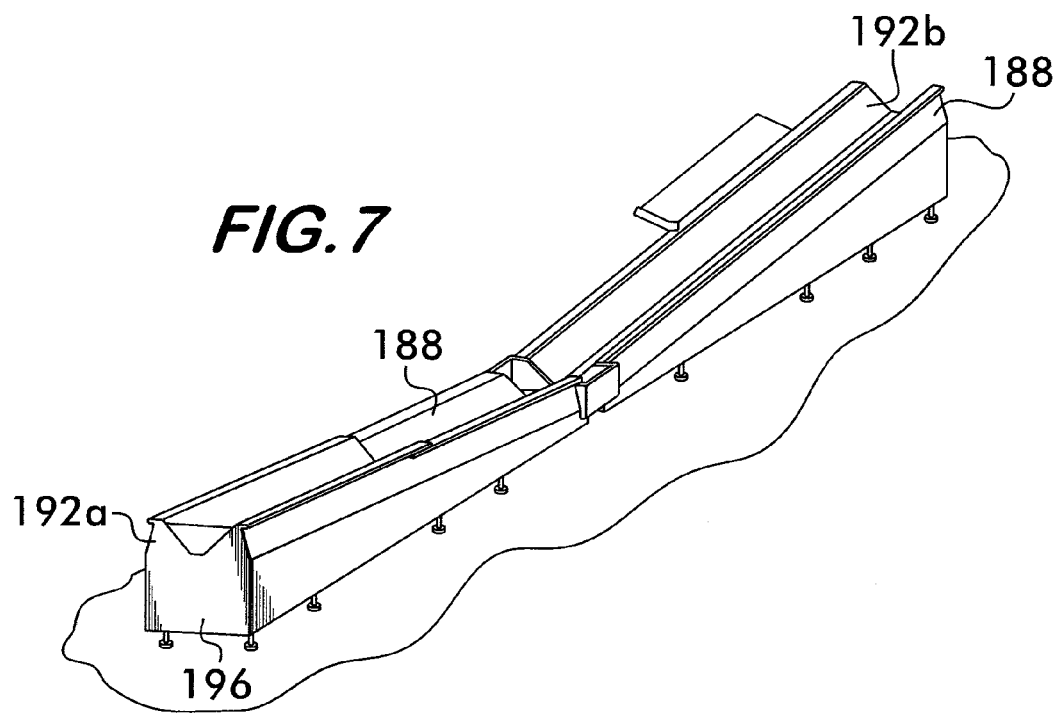
FIG. 7 is an isometric view of the drain trough from the drainage station.
Figure 7A:
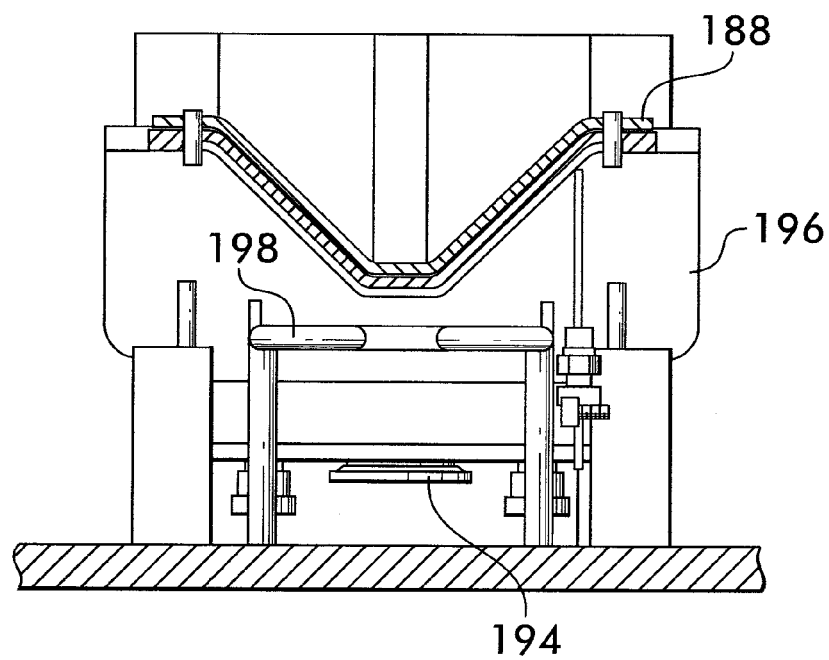
FIG. 7A is a cross-sectional view of the drain trough of FIG. 7.

With further reference to FIGS. 1B, 7, and 7A, the trough is "V" shaped in cross section as shown, is sloped from both ends 192a, 192b towards a central trough drain port 194 where there is a funnel, and rests on a trough base 196. The trough is made of suitable material such as stainless steel and can be optionally cooled by glycol-chilled tubes 198 running underneath the trough base to cool the allantoic fluid if desired. The drain port 194 connects to a fluid connection vessel 195 stored in the access area 200 (FIG. 1B) from which the fluid can be pumped for further processing. The trough 188 is sufficiently long to obtain as much of the allantoic fluid as reasonably possible. Although a range of time from about 40 to about 90 seconds for an egg to drain over the trough is believed to be a good time, a more preferable range is from about 60 to about 65 seconds which is believed to be a good balance to collect as much fluids as possible without collecting too much unwanted materials (e.g., yolk, blood, albumen, etc.)

Figure 7B:
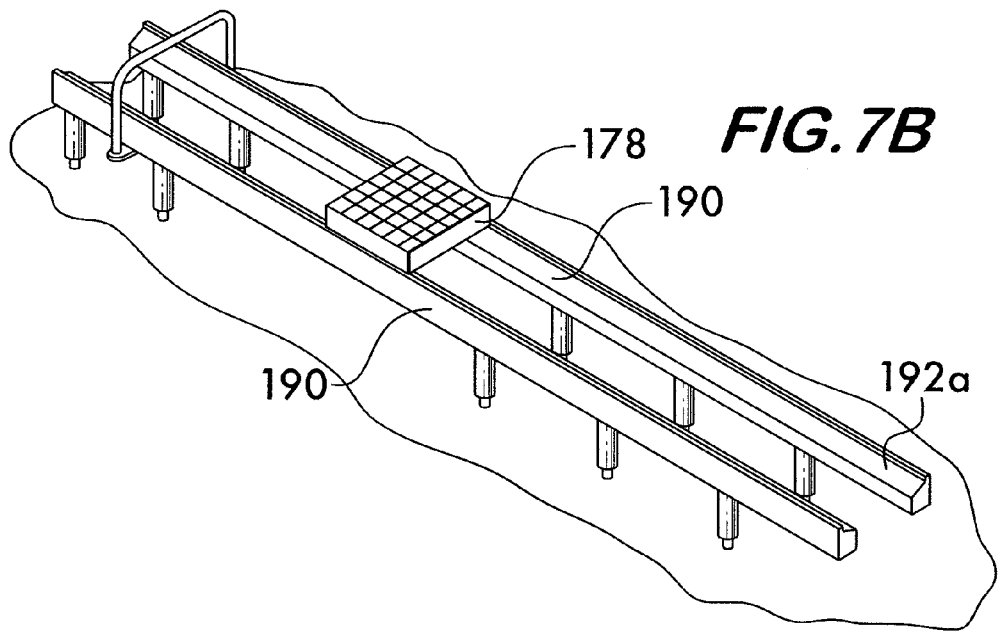
FIG. 7B is an isometric view of the guide rail in the drainage station.
Figure 7C:
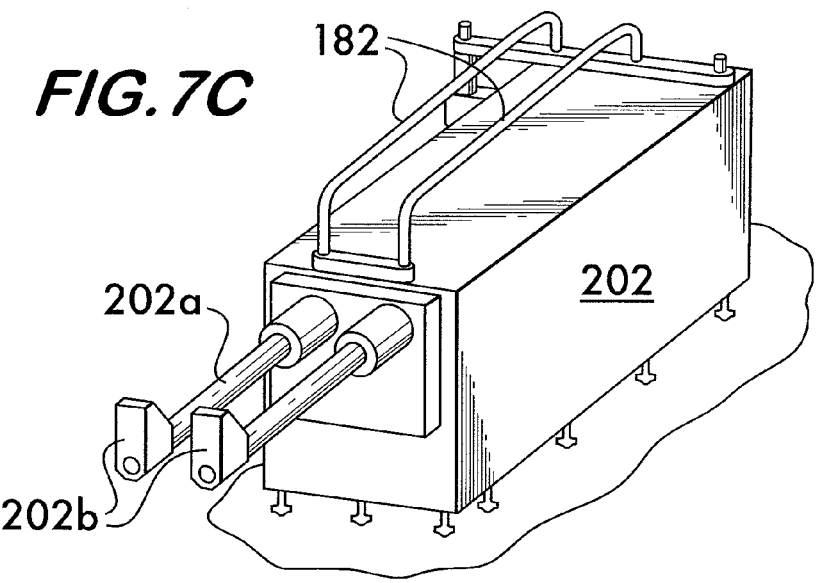
FIG. 7C is an isometric view of the tray/pan indexer.
Figure 7D:
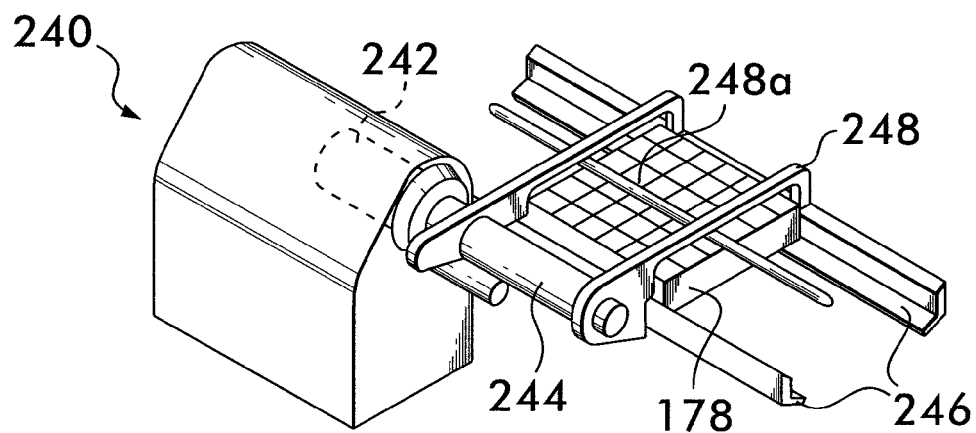
FIG. 7D is an isometric view of a tray tilter.
Figure 7E:
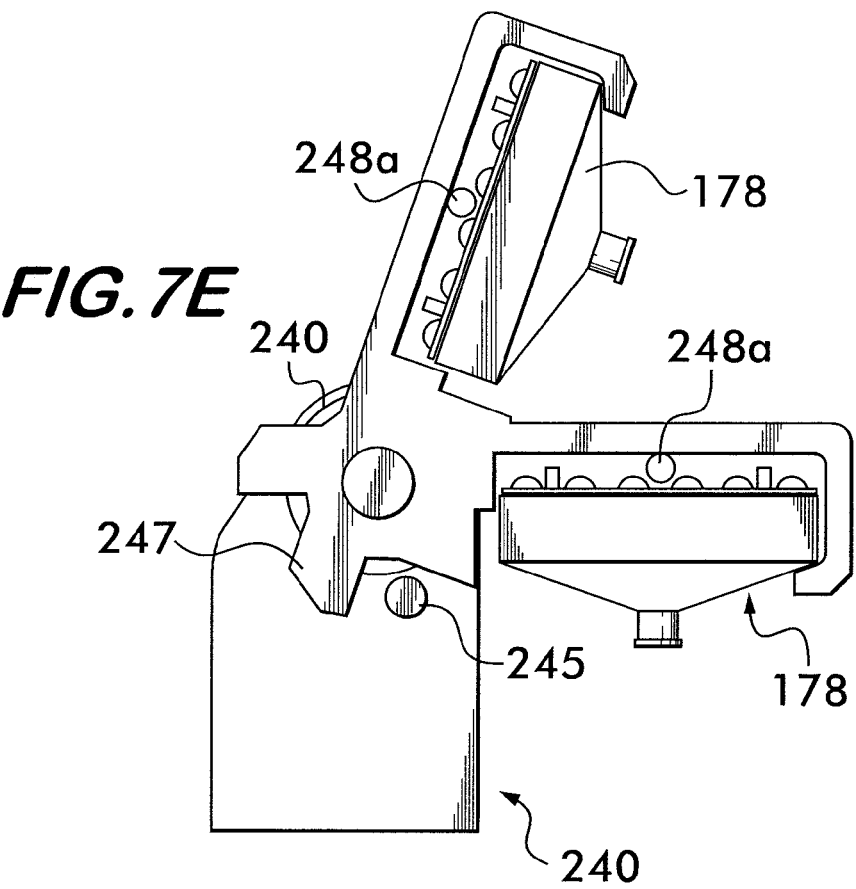
FIG. 7E is a side view showing the tray tilter of FIG. 7D tilting a tray.

The guide rails 190 extend over the entire trough and are made of a suitable material to allow the metal pan surface to slide over it, such as UHMW (See FIG. 7B showing the rails removed from the trough). The inverted tray pans 178 are moved onto the guide rails 190 directly from the invert unit 180, thus one end 192a of the rails is adjacent the invert unit 180 and positioned to receive the inverted tray/pan assemblies 178 directly therefrom. With reference to FIG. 7C, tray/pan indexer 202 is positioned underneath the load invert unit and has pusher arms 202a and pusher fingers 202b that rotate upward to engage the tray posts 44a while the tray/pan is still within the static rails 184 and 186 of the inverter unit, and then push the tray/pan 178 from the static arms of the invert unit onto the guide rails 190 over the drain trough. As the tray/pans contact each other, the continuous action of the tray/pan indexer 202 moves the tray/pans over the entire length of the trough towards the outfeed pan and invert station 32. With reference to FIGS. 6, 6A, and 7C, it is seen that the indexer 202 is located under the infeed pan and invert station 28 and supports the rails 182 on which the trays 36 and tray/pan assemblies 178 slide up until the invert of the tray/pan 178.

It is believed that some amount of jarring, vibration or other such movement of the eggs may help release additional allantoic fluid that might not normally drain out, or at least help speed up the draining process. One possibility is an optional tray tilter 240 capable of tilting three tray/pans 178 at the same time. With reference to FIGS. 1, 1B, 7D and 7E, the tray tilter 240 is has a servo motor 242 driving a shaft 244 connected to tilt rails 246 which are adjacent to and align with the guide rails 190 of the collection trough 188 to receive tray/pans 178 therefrom. The collection trough is extended under the tilter to collect any fluid from the tray/drain pans 178. The tilter 240 further includes tray hold down members 248 to help keep the trays in place on the rails during the tilt action, one being a bar 248a positioned over the back side of the tray 36 between a row of eggs. In use, three tray/pans 178 can be moved into the tray tilter on the rails 246 (only one being shown in the center position in FIG. 7D) and once in proper position, the servo motor tilts the tray/pan 178 and then immediately returns it to its starting position so that any additional fluid can drain. In the preferred embodiment, the tilter 240 can tilt the pans to an angle from about 0° to about 85° and more preferably to at least about 82 degrees from the horizontal, at a tilt servo speed preferably of at least about 250°/s, and with a pant tilt servo acceleration preferably of less than about 505°/s² although other specifications are believed suitable depending on the particular design. A stop 245 can help control the movement of the shaft 244 with stop plate 247. Here, the direction of tilt is perpendicular to the direction of the pan motion. The tilter can be turned off allowing the tray/pans 178 to pass through to the next station. Any suitable indexer may be used to move the tray/pans 178 into and out of the tilter, including relying on the index servo moving the tray/pans over the collection trough. Any other suitable means of obtaining additional fluids can be used, one such means might include inducing vibrations into the eggs.

Figure 8:
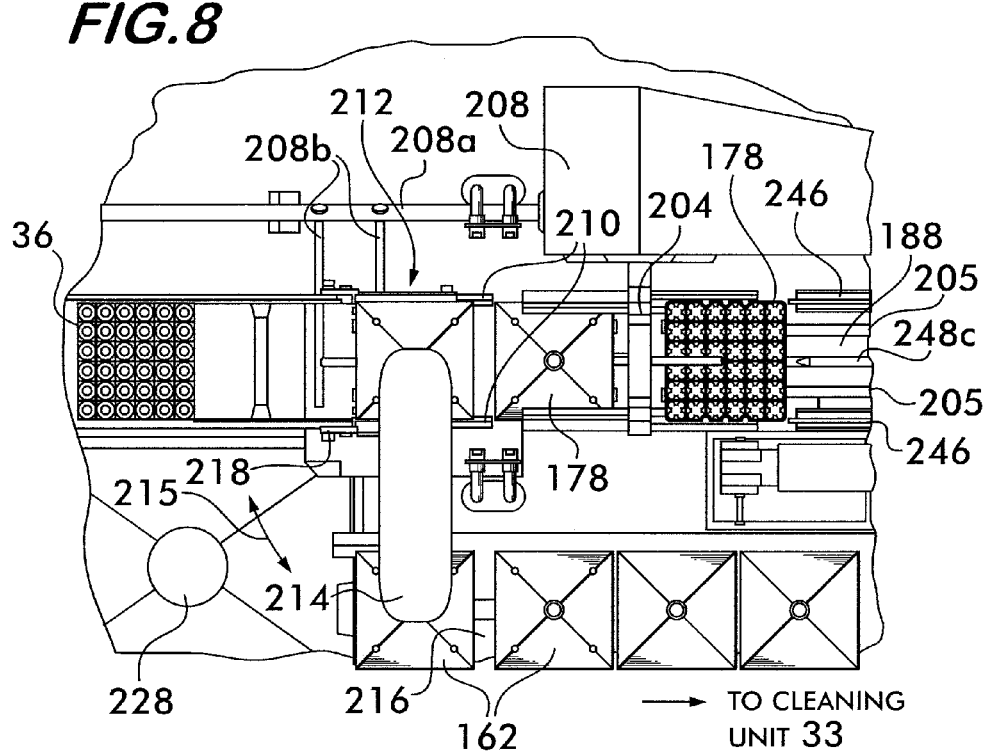
FIG. 8 is a top view of the outfeed pan and invert station.

At the outfeed pan and invert station 32, and with reference to FIGS. 1, 1B and 8 the tray/pan 178 is re-inverted so that the drain pan 162 can be removed and sent to the rinse unit 33. Near the end of the drainage trough 188, the trays are moved into a second inverter unit 204 on guide rails 205 by another index servo 206 which is similar to the index servo 172 discussed above with reference to FIGS. 6, 6A and 6C. The inverter unit 204 is similar in construction to the inverter unit 180 discussed previously, re-inverting the tray/pan 178 so that the pan 162 is again on top (semicircle 29a in FIG. 1 indicating the inversion motion).

Once inverted, the tray/pan 178 is indexed forward by an index servo 208 having a walking beam 208a with 4 arms 208b (see FIGS. 1 and 1B) and posts 208c thereon for moving 4 trays simultaneously downstream of the inverter 204 (by engaging the tray posts 44a). Thus, with one index movement, it moves a re-inverted tray from the inverter 204 onto rails 210 and into the pan pick up position 212, an adjacent tray (not shown) from the pan pick up station 212 one index movement forward on the rails 210, and also moves the next two adjacent trays one index movement forward on the rails 210 into and then out of the tray dump system 220.

At pick up position 212, a second pick and place unit 214, similar in construction, components and operation as the pick and place unit 170 described previously, picks the drain pan 162 up off the tray 36 and rotates in the direction 215 to place the drain pan on an infeed conveyor 216 that moves the pans into the rinse unit 33 where the pans are rinsed and conveyed to the infeed pan and invert station 28 for re-use. Mechanical stops 218 engage the pan to prevent the pan/tray 178 from traveling past the pick up position 212, the stop 218 being positioned to stop only the pan as once the pan is lifted the tray can move to the next position without interference from the stop.

Figure 8A:
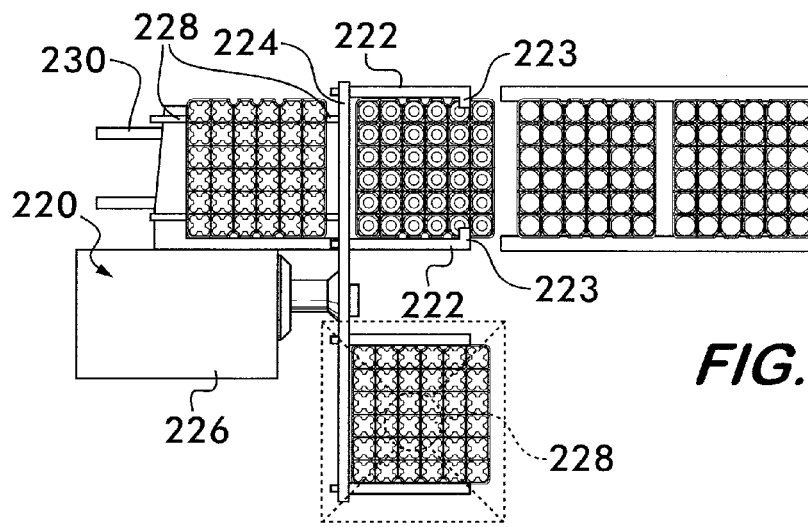
FIG. 8A is a top view of the tray dump system.

With further reference to FIGS. 8 and 8A, after removal of the drain pan from the tray 36, the tray is indexed forward to a tray dump system 220 by the servo index unit 208. The tray dumping system includes two tray clamp rails 222 into which the tray 36 is slidably moved by the index servo 208. The tray clamp rails 222 have hold down members 223 positioned to be just above the registration projections 44 of the tray to hold the tray in place during inverting. A dump servo 226, connected to clamp rails 222 by arm 224, rotates to invert the tray over a waste dump 228 where the remaining debris (eggs) is disposed. Any suitable combination of characteristics of the dump system, such as velocity, acceleration and angle of the tray, can be chosen to remove the eggs from the tray. The dump servo then reverses rotation to return the emptied tray 36 for a final index movement by the index servo 208 from the tray dump system onto slide rails 228, and then the tray is finally pushed by the trays behind it into the tray outfeed station 34 where the trays are conveyed through any known means, such as by moving conveyor belts 230 as shown, from the apparatus 20 for collection and cleaning as may be desired for reuse.

Sensors, controllers, and other electronics as known in the art can be used to control the movements and processes of the apparatus 20.

It is understood that the foregoing description is intended to describe a preferred embodiment of the present invention, and is not intended to limit the invention in any way. For example, it is appreciated that use of a differently configured egg tray, or one having a different number of eggs, might require modifications and alterations from the preferred embodiment described above. It is further appreciated that the term tray can mean any device for holding multiple eggs. Similarly, the number and configuration of the de-cap units could be changed, the construction of the egg lifting components (e.g., directly coupled lifting arms rather than magnetically coupled arms), and alternative means of moving and conveying the trays could be employed. Suitable servo motors, actuators, and other mechanical and/or fluidic powered drive mechanisms may be substituted without affecting the operation of particular parts of apparatus 20 based on routine experimentation. It is further appreciated that the various devices and methods of transporting the eggs through the apparatus 20 comprises an egg transport system that can be formed of any suitable device or combination of devices and systems as known in the art.

What is claimed is:

1. An apparatus for de-capping an egg, comprising:
a reference plate having at least one reference opening therethrough, said opening being configured for receiving said egg therein from a lower side of said plate and for stopping further upward movement of said egg within said opening when an upper egg section to be cut extends from said opening above said first plate;
a cutter member positioned above said reference plate, said cutter member being moveable across said reference opening so as to create an opening in said upper egg section;
a cleaning member moveable above said reference plate for removing egg debris; and
wherein said reference plate includes a debris opening adjacent to said reference opening; and said cleaning member is configured to move said egg debris towards said debris opening.

2. An apparatus for de-capping an egg in accordance with claim 1, wherein said cutter member includes at least one blade which is reciprocal between a precut position where said blade is adjacent to said reference opening, and a post cut position where said blade has moved over said reference opening to create said opening in said egg.

3. An apparatus for de-capping an egg in accordance with claim 1 further comprising a lifter arm positioned below said reference opening and configured for holding an egg, said lifter arm being moveable to move an egg upward into said reference opening, and moveable downward to remove said egg from said reference opening.

4. An apparatus for de-capping an egg in accordance with claim 3 wherein said lifter arm is magnetically coupled to a coupler piston, said lifter arm moving in response to movement of said coupler piston.

5. An apparatus for collecting fluid from multiple eggs, comprising: at least one de-cap apparatus in accordance with claim 1; a invert unit for inverting said eggs to face downward to allow said fluid to drain therefrom; a drainage trough for collecting draining fluids from said inverted eggs; and a transport system for moving said multiple eggs from said de-cap station to said invert station and to said drainage trough.

6. The apparatus of claim 5 further comprising a tray for holding said multiple eggs, said tray being moveable through said apparatus via said transport system.

7. An apparatus for collecting fluid from multiple eggs, comprising:
at least one de-cap apparatus comprising a reference plate having at least one reference opening therethrough, said opening being configured for receiving said egg therein from a lower side of said plate and for stopping further upward movement of said egg within said opening when an upper egg section to be cut extends from said opening above said first plate; a cutter member positioned above said reference plate, said cutter member being moveable across said reference opening so as to create an opening in said upper egg section; and a cleaning member moveable above said reference plate for removing egg debris;
an invert unit for inverting said eggs to face downward to allow said fluid to drain therefrom; a drainage trough for collecting draining fluids from said inverted eggs;
a transport system for moving said multiple eggs from said de-cap station to said invert station and to said drainage trough;
a tray for holding said multiple eggs, said tray being moveable through said apparatus via said transport system; and
a drainage pan configured to fit over said tray to form a tray/pan assembly, said pan having a drainage opening through which fluid can drain, and said invert unit being configured to invert said tray/pan assembly so as to invert the eggs therein.

8. The apparatus of claim 7 wherein said drainage pan includes retaining members configured to perforate an allantoic membrane within said eggs and positioned to hold embryos within said eggs when said eggs are inverted.

9. The apparatus of claim 7 further comprising: multiple egg lifter arms for moving said eggs from said tray to said de-cap apparatus, said arms being configured for holding the eggs and are attached to an actuator to move said arms between said tray and said de-cap apparatus; and a pick and place device for placing a drain pan on top of said tray to form a tray/pan unit.

10. An apparatus for collecting fluid from multiple eggs, comprising:
a. at least one de-cap apparatus; comprising a reference plate having at least one reference opening therethrough, said opening being configured for receiving said egg therein from a lower side of said plate and for stopping further upward movement of said egg within said opening when an upper egg section to be cut extends from said opening above said first plate; a cutter member positioned above said reference plate, said cutter member being moveable across said reference opening so as to create an opening in said upper egg section; and a cleaning member moveable above said reference plate for removing egg debris;

b. at least one tray configured for holding said multiple eggs therein;

c. lifting arms configured to hold said eggs, said arms being operable to lift said eggs from said tray and move them to said de-cap unit and then return said eggs to said tray;

d. a drainage pan configured to be combined with said tray to form a tray/pan assembly;

e. a invert unit for inverting said tray/pan assembly so that the openings of said eggs therein face downward to allow said fluid to drain therefrom;

f. a drainage trough for collecting draining fluids from said inverted eggs, said inverted tray/pan assembly being moveable over said trough; and g. a transport system for moving said tray and tray/pan assembly through said apparatus.

11. The apparatus of claim 1, further comprising a debris removal channel positioned proximate to the debris opening to receive debris therein.

12. The apparatus of claim 11, further comprising apparatus delivering a blast of compressed gas to the debris removal channel.

* * * * *